US005079163A

United States Patent [19]

Piatak, Jr. et al.

[11] Patent Number: 5,079,163

[45] Date of Patent: Jan. 7, 1992

[54] RECOMBINANT RICIN TOXIN FRAGMENTS

[75] Inventors: Michael Piatak, Jr., Walnut Creek; L. L. Houston; Anne W. Emerick, both of Oakland, all of Calif.

[73] Assignee: Cetus Corporation, Emeryville, Calif.

[21] Appl. No.: 25,262

[22] Filed: Mar. 12, 1987

Related U.S. Application Data

[63] Continuation-in-part of Ser. No. 717,319, Mar. 29, 1985, which is a continuation-in-part of Ser. No. 578,121, Feb. 8, 1984, abandoned.

[51] Int. Cl.[5] ...................... C12N 1/21; C12N 15/70; C07K 13/00

[52] U.S. Cl. ............................ 435/252.3; 435/320.1; 530/396

[58] Field of Search ................ 435/68, 70, 172.3, 91, 435/320, 252.3, 320.1; 530/396, 377, 370; 536/27

[56] References Cited

FOREIGN PATENT DOCUMENTS 0169006 1/1986 European Pat. Off. .
0196762 10/1986 European Pat. Off. .

OTHER PUBLICATIONS

Wawrzynczak, E. J. et al, Feb. 22, 1986, J. Cell. Bioch. 10B: p. 71.
Robertus, J. D. et al, Jan. 5, 1987, J. B.C. 262(1), 19–20.
Lamb, F. I. et al, 1985, Eur. J. Biochem. 148:265–270.
Zoller, M. J. and Smith, M., 1984, DNA 3(6), 479–488.
Mise, T. et al, 1986, Agric. Biol. Chem. 50(1), 151–155.
Zoller, M. J. and Smith, M., 1982, Nucl. Acids Res. 10(20), 6487–6500.
Montfort, W. et al., Apr. 15, 1987, J. B.C. 262(11), 5398–5403.
Rutenber, E. et al, 1987 (Apr. 9), Nature 326:1624–1626.
Ladin, B. F. et al., 1987, *Plant Molecular Biology*, 9:287–295.
Halling, K. C., et al., 1985, *Nucleic Acids Research*, 13 (22):8019–8032.

*Primary Examiner*—Richard A. Schwartz
*Attorney, Agent, or Firm*—Gregory J. Giotta; Elliott Fineman; Albert P. Halluin

[57] ABSTRACT

Ricin B muteins, ricin and ricin precursors having at least one amino acid of at least one galactoside binding site altered to decrease the binding of ricin B to galactosides are claimed. DNA sequences encoding the ricin B muteins, ricin and ricin precursor in which the B chain thereof is the ricin B mutein are claimed. Recombinant expression vectors effective in expressing the DNA sequences of the ricin B muteins, ricin and ricin precursors are claimed. Host cells transformed with the foregoing expression vectors are also claimed. Conjugates comprising binding moieties such as antibodies, hormones, and lymphokines bound to the ricin B mutein and ricin wherein the B chain thereof is the mutein is also claimed.

11 Claims, 12 Drawing Sheets

FIG. 3

Comparison of Ricin-B Sequence with RTB-5

```
R-AlaAspValCysMetAspProGluProIleValArgIleValGlyArgAsnGlyLeuCys
                                      ArgIleValGlyArgAsnGlyLeuCys
                              gaattccGCGTATCGTAGGTCGAAATGGTCTATGT

R-ValAsnValArgAspGlyArgPheAsnHisGlyAsnAlaIleGlnLeuTrpProCysLys
  ValAspValArgAspGlyArgPheHisAsnGlyAsnAlaIleGlnLeuTrpProCysLys
  GTTGATGTTAGGGATGGAAGATTCCACAACGGAAACGCAATACAGTTGTGGCCATGCAAG

R-SerAsnThrAspAlaAsnGlnLeu   ThrLeuLysArgAspAsnThrIleArgSerAsn
  SerAsnThrAspAlaAsnGlnLeuTrpThrLeuLysArgAspAsnThrIleArgSerAsn
  TCTAATACAGATGCAAATCAGCTCTGGACTTTGAAAAGAGACAATACTATTCGATCTAAT

R-GlyLysCysLeuThrThrTyrGlyTyrProSerGlyValTyrValMetIleTyrAspCys
  GlyLysCysLeuThrThrTyrGlyTyrSerProGlyValTyrValMetIleTyrAspCys
  GGAAAGTGTTTAACTACTTACGGGTACAGTCCGGGAGTCTATGTGATGATCTATGATTGC

R-AsnThrAlaAlaThrThrAlaAspArg   GluIleTrpAsnAsnGlyThrIleIleAsnPro
  AsnThrAlaAlaThrAspAlaThrArgTrpGlnIleTrpAspAsnGlyThrIleIleAsnPro
  AATACTGCTGCAACTGATGCCACCCGCTGGCAAATATGGGATAATGGAACCATCATAAATCCC

R-ArgSerSerLeuValLeuAlaAlaThrSerGlyAsnSerGlyThrThrLeuThrValGlnThr
  ArgSerGlyLeuValLeuAlaAlaThrSerGlyAsnSerGlyThrThrLeuThrValGlnThr
  AGATCTAGTCTAGTTTTAGCAGCGACATCAGGCAACAGTGGTACCACACTTACAGTGCAAACC

R-AsnIleTyrAlaValSerGlnGlyProLeuPheThrAsnAsnThrGlnProTrpValThr
  AsnIleTyrAlaValSerGlnGlyTrpLeuProThrAsnAsnThrGlnProPheValThr
  AACATTTATGCCGTTAGTCAAGGTTGGCTTCCTACTAATAATACACAACCTTTTGTGACA

R-ThrIleValGlyLeuTyrGlyLeuCysLeuGlnAlaAsnSerGlyGlnValValIleGlu
  ThrIleValGlyLeuTyrGlyLeuCysLeuGlnAlaAsnSerGlyGlnValTrpIleGlu
  ACCATTGTTGGGCTATACGGTCTGTGCTTGCAAGCAAATAGTGGACAAGTATGGATAGAG

R-AspSerCysSerGluLysAlaGluGlnGlnTrpAlaLeuTyrAlaSerGlyAsnIleAsn
  AspCysSerSerGluLysAlaGluGlnGlnTrpAlaLeuTyrAlaAspGlySerIleArg
  GACTGTAGCAGTGAAAAGGCTGAACAACAGTGGGCTCTTTATGCAGATGGTTCAATACGT

R-ProGlnGlnArgArgAspAsnCysLeuThrSerAspSerAsnIleArgGluThrValVal
  ProGlnGlnAsnArgAspAsnCysLeuThrSerAspSerAsnIleArgGluThrValVal
  CCTCAGCAAAACCGAGATAATTGCCTTACAAGTGATTCTAATATACGGGAAACAGTTGTC

R-LysIleLeuSerCysGlyProAlaSerSerGlyGluArgTrpMetPheLysAsnAspGly
  LysIleLeuSerCysGlyProAlaSerSerGlyGlnArgTrpMetPheLysAsnAspGly
  AAGATCCTCTCTTGTGGCCCTGCATCCTCTGGCCAACGATGGATGTTCAAGAATGATGGA

R-ThrIleLeuAsnLeuTyrSerGlyLeuValLeuAspValArgAlaSerAspProSerLeu
  ThrIleLeuAsnLeuTyrSerGlyLeuValLeuAspValArgAlaSerAspProSerLeu
  ACCATTTTAAATTTGTATAGTGGGTTGGTGTTAGATGTGAGGGCATCGGATCCGAGCCTT

R-LysGlnIleIleLeuTyrProLeuTrpGlyHisAspProAsnGlnLeu   IleLeuProPhe
  LysGlnIleIleLeuTyrProLeu   HisGlyAspProAsnGlnIleTrpLeuProLeuPheTerTer
  AAACAAATCATTCTTTACCCTCTC   CATGGTGACCCAAACCAAATATGGTTACCATTATTTTGATAG

  ACAGATTACTCTCTTGCAGTGTGTATGTCCTGCCATGAAAATAGATGGCTTAAATAAAAA
  GGACATTGTAAATTTTGTAACTGAAAGGACAGCAAGTTATTGCAGTCCAGTATCTAATAA
  GAGCACAACTATTGTCTTGTGCAAAAAA....
```

FIG. 2

Ricin-B Protein Sequence

AlaAspValCysMetAspProGluProIleValArgIleValGlyArgAsnGlyLeuCys
ValAsnValArgAspGlyArgPheAsnHisGlyAsnAlaIleGlnLeuTrpProCysLys
SerAsnThrAspAlaAsnGlnLeuThrLeuLysArgAspAsnThrIleArgSerAsnGly
LysCysLeuThrThrTyrGlyTyrProSerGlyValTyrValMetIleTyrAspCysAsn
ThrAlaAlaThrThrAlaAspArgGluIleTrpAsnAsnGlyThrIleIleAsnProArg
SerSerLeuValLeuAlaAlaThrSerGlyAsnSerGlyThrThrLeuThrValGlnThr
AsnIleTyrAlaValSerGlnGlyProLeuPheThrAsnAsnThrGlnProTrpValThr
ThrIleValGlyLeuTyrGlyLeuCysLeuGlnAlaAsnSerGlyGlnValValIleGlu
AspSerCysSerGluLysAlaGluGlnGlnTrpAlaLeuTyrAlaSerGlyAsnIleAsn
ProGlnGlnArgArgAspAsnCysLeuThrSerAspSerAsnIleArgGluThrValVal
LysIleLeuSerCysGlyProAlaSerSerGlyGluArgTrpMetPheLysAsnAspGly
ThrIleLeuAsnLeuTyrSerGlyLeuValLeuAspValArgAlaSerAspProSerLeu
LysGlnIleIleLeuTyrProLeuTrpGlyHisAspProAsnGlnLeuIleLeuProPhe (260 a.a -- from Funatsu)

FIG. 4a

Sequences of pRTA-115, pRTB-4 and pRTB-5 Cloned Inserts

115-TATTAATCCCTATCATAGCTCTCATGGTGTATAGATGCGCACCTCCACCGTCGTCACAGTT

115-TTCTTTGCTTATAAGGCCAGTGGTGCCAAATTTTAATGCTGATGTTTGTATGGATCCTGAGC

RTA-115 <-(EcoRI)-> RTB-4

115-CCATAGTGCGTATCGTAGGTCGAAATGGTCTATGTGTTGATGTTACAGGTGAAGAATTCTAC<br>
5-gaattccGCGTATCGTAGGTCGAAATGGTCTATGTGTTGATGTTAGGGATGGAAGATTCCAC 4-GATGGAAACCCAATACAATTGTGGCCTTGCAAATCTAATACAGACTGGAATCAGTTATGGA<br>
5-AACGGAAACGCAATACAGTTGTGGCCATGCAAGTCTAATACAGATGCAAATCAGCTCTGGA 4-CTTTGAGAAAAGACGGTACAATTCGATCTAATGGCAAGTGTTTGACCATTTATAAGTCCAG<br>
5-CTTTGAAAAGAGACAATACTATTCGATCTAATGGAAAGTGTTTAACTACTTACGGGTACAG 4-TCTAGGAAAGCATGTGATGATATATAATTGTACTACCGCTACAGTTGGTGCCACCCGTTGG<br>
5-TCCGGGAGTCTATGTGATGATCTATGATTGCAATACTGCTGCAACTGATGCCACCCGCTGG 4-CAAATATGGGACAACCGAACCATCATAAATCCCATATCTGGTTTAGTTTTGGCAGCCACAT<br>
5-CAAATATGGGATAATGGAACCATCATAAATCCCAGATCTAGTCTAGTTTTAGCAGCGACAT 4-CAGGAAACAGTGGTACCACACTTACAGTGCAAACCAACATTTATGCCGTTAGTCAAGGTTG<br>
5-CAGGCAACAGTGGTACCACACTTACAGTGCAAACCAACATTTATGCCGTTAGTCAAGGTTG 4-GCTTCCTAGTAATAATACACAACCTTTTGTGACATCCATTGTTGGGCTAAATGATCTCTGT<br>
5-GCTTCCTACTAATAATACACAACCTTTTGTGACAACCATTGTTGGGCTATACGGTCTGTGC 4-TTACAAGCAAATACTGGAAAAGTATGGTTAGACGAGTGTACAAGTGAAAAGGCTGAACAAC<br>
5-TTGCAAGCAAATAGTGGACAAGTATGGATAGAGGACTGTAGCAGTGAAAAGGCTGAACAAC 4-AATGGGCGCTTTATGCAGATGGTTCAATACGGCCTCAGCAAAACCAAGATAACTGCCTTAC<br>
5-AGTGGGCTCTTTATGCAGATGGTTCAATACGTCCTCAGCAAAACCGAGATAATTGCCTTAC 4-AAGTGATGCTAATATACGAGAAACAATTGTCAAGACCCTCTCTTGCAGCACTGCATCCTCC<br>
5-AAGTGATTCTAATATACGGGAAACAGTTGTCAAGATCCTCTCTTGTGGCCCTGCATCCTCT 4-GGCCAGCGATGGATGTTCAAGAATGATGGAACCATTTGGAATTTGTATAATGGATTGGTGT<br>
5-GGCCAACGATGGATGTTCAAGAATGATGGAACCATTTTAAATTTGTATAGTGGGTTGGTGT 4-TAGATGTGAAGCGATCGGATCCGACCCTTAAACAAATCATTATTTACCCTTTCCATGGAAA<br>
5-TAGATGTGAGGGCATCGGATCCGAGCCTTAAACAAATCATTCTTTACCCTCTCCATGGTGA 4-CCCAAACCAAATATGGTTTCCACTATTTTGATAGACTAATTACCCTCTTGCAGTGTATGTA<br>
5-CCCAAACCAAATATGGTTACCATTATTTTGATAGACAGATTACTCTCTTGCAGTGTGTATG 4-TGTCCTACCATGAACATAGTTG CTTAAATAAAAAGGACATTGTAAATTAAAAAAA...<br>
5- TCCTGCCATGAAAATAGATGGCTTAAATAAAAAGGACATTGTAAATTTTGTAACTGAAA

5-GGACAGCAAGTTATTGCAGTCCAGTATCTAATAAGAGCACAACTATTGTCTTGTGCAAAAAA...

FIG. 4b

Comparison of Translated Protein of RTB4 to RTB5

```
RTB-4: GAATTCTACGATGGAAACCCAATACAATTGTGGCCTTGCAAATCTAATACAGACTGGAAT
RTB-4: GluPheTyrAspGlyAsnProIleGlnLeuTrpProCysLysSerAsnThrAspTrpAsn
RTB-5: ArgPheHisAsnGlyAsnAlaIleGlnLeuTrpProCysLysSerAsnThrAspAlaAsn

       CAGTTATGGACTTTGAGAAAAGACGGTACAATTCGATCTAATGGCAAGTGTTTGACCATT
     4-GlnLeuTrpThrLeuArgLysAspGlyThrIleArgSerAsnGlyLysCysLeuThrIle
     5-GlnLeuTrpThrLeuLysArgAspAsnThrIleArgSerAsnGlyLysCysLeuThrThr

       TATAAGTCCAGTCTAGGAAAGCATGTGATGATATATAATTGTACTACCGCTACAGTTGGT
     4-TyrLysSerSerLeuGlyLysHisValMetIleTyrAsnCysThrThrAlaThrValGly
     5-TyrGlyTyrSerProGlyValTyrValMetIleTyrAspCysAsnThrAlaAlaThrAsp

       GCCACCCGTTGGCAAATATGGGACAACCGAACCATCATAAATCCCATATCTGGTTTAGTT
     4-AlaThrArgTrpGlnIleTrpAspAsnArgThrIleIleAsnProIleSerGlyLeuVal
     5-AlaThrArgTrpGlnIleTrpAspAsnGlyThrIleIleAsnProArgSerGlyLeuVal

       TTGGCAGCCACATCAGGAAACAGTGGTACCACACTTACAGTGCAAACCAACATTTATGCC
     4-LeuAlaAlaThrSerGlyAsnSerGlyThrThrLeuThrValGlnThrAsnIleTyrAla
     5-LeuAlaAlaThrSerGlyAsnSerGlyThrThrLeuThrValGlnThrAsnIleTyrAla

       GTTAGTCAAGGTTGGCTTCCTAGTAATAATACACAACCTTTTGTGACATCCATTGTTGGG
     4-ValSerGlnGlyTrpLeuProSerAsnAsnThrGlnProPheValThrSerIleValGly
     5-ValSerGlnGlyTrpLeuProThrAsnAsnThrGlnProPheValThrThrIleValGly

       CTAAATGATCTCTGTTTACAAGCAAATACTGGAAAAGTATGGTTAGACGAGTGTACAAGT
     4-LeuAsnAspLeuCysLeuGlnAlaAsnThrGlyLysValTrpLeuAspGluCysThrSer
     5-LeuTyrGlyLeuCysLeuGlnAlaAsnSerGlyGlnValTrpIleGluAspCysSerSer

       GAAAAGGCTGAACAACAATGGGCGCTTTATGCAGATGGTTCAATACGGCCTCAGCAAAAC
     4-GluLysAlaGluGlnGlnTrpAlaLeuTyrAlaAspGlySerIleArgProGlnGlnAsn
     5-GluLysAlaGluGlnGlnTrpAlaLeuTyrAlaAspGlySerIleArgProGlnGlnAsn

       CAAGATAACTGCCTTACAAGTGATGCTAATATACGAGAAACAATTGTCAAGACCCTCTCT
     4-GlnAspAsnCysLeuThrSerAspAlaAsnIleArgGluThrIleValLysThrLeuSer
     5-ArgAspAsnCysLeuThrSerAspSerAsnIleArgGluThrValValLysIleLeuSer

       TGCAGCACTGCATCCTCCGGCCAGCGATGGATGTTCAAGAATGATGGAACCATTTGGAAT
     4-CysSerThrAlaSerSerGlyGlnArgTrpMetPheLysAsnAspGlyThrIleTrpAsn
     5-CysGlyProAlaSerSerGlyGlnArgTrpMetPheLysAsnAspGlyThrIleLeuAsn

       TTGTATAATGGATTGGTGTTAGATGTGAAGCGATCGGATCCGACCCTTAAACAAATCATT
     4-LeuTyrAsnGlyLeuValLeuAspValLysArgSerAspProThrLeuLysGlnIleIle
     5-LeuTyrSerGlyLeuValLeuAspValArgAlaSerAspProSerLeuLysGlnIleIle

       ATTTACCCTTTCCATGGAAACCCAAACCAAATATGGTTTCCACTATTTTGATAGACTAAT
     4-IleTyrProPheHisGlyAsnProAsnGlnIleTrpPheProLeuPhe
     5-LeuTyrProLeuHisGlyAspProAsnGlnIleTrpLeuProLeuPhe

       TACCCTCTTGCAGTGTATGTATGTCCTACCATGAACATAGTTGCTTAAATAAAAAGGACA

       TTGTAAATTAAAAAAAAAAAAAAAAA
```

FIG. 5a Junction Region for the Construction of pRTB601

```
                                                            |-----    pRTB-151    --->
       Hind III  |-------------    ricin-B    --------------------------->
                 MetAlaAspValCysMetAspProGluProIleValArgIleValGlyArgAsnGlyLeu...
GACCATGATAAGCTTATGGCTGATGTTTGTATGGATCC           GCGTATCGTAGGTCGAAATGGTCTA...
                                TACCTAGGACTCGGGTATCACGCATAGCATCC       ACCAGAT...
       (oligo 2)                         (oligo 1)
```

FIG. 5b Fusion of lacZ and Ricin-B in pRTB236

```
  <-----  lacZ  ----------|  |----------   ricin-B   --------------->
                 MetThrMetIleThrProArgIleValGlyArgAsnGlyLeuCysValAspValArgAsp...
...CAGGAAACAGCTATGACCATGATTACGCCGCGTATCGTAGGTCGAAATGGTCTATGTGTTGATGTTAGGGAT...
  (RBS)
```

FIG. 5c Junction Region in pRTB514

```
                                  |----------   ricin-B   ------------->
  <-----   pDG141   -------||-------------   pRTB601   ---------------->
                                  MetAlaAspValCysMetAspProGluProIleValArgIle...
...AGTTCACGTAAAAAGGGTATCGATAAGCTTATGGCTGATGTTTGTATGGATCCTGAGCCCATAGTGCGTATC...
              (RBS)     Hind III
```

Key 1 natural ricin-B 2 pUC8

3 pRTB5

4 pRTB151

5 pRTB221

6 pRTB236

7 pRTB514

8 pRTB704

9 pRTB907

```
                                             Sal 1
                                             GTCGAC
5'                                  GGTCTATGTGTCGACGTTAGGG  oligonucleotide
CCCATAGTGCGTATCGTAGGTCGAAATGGTCTATGTGTTGATGTTAGGGATGGAAGATTC
---------+---------+---------+---------+---------+---------+ 1020
GGGTATCACGCATAGCATCCAGCTTTACCAGATACACAACTACAATCCCTACCTTCTAAG
3'                                           CAGCTG
P  I  V  R  I  V  G  R  N  G  L  C  V  D  V  R  D  G  R  F  -
  10             15             20             25

                                                          Pvu 2
                                                          CAGCTG
5'                                                   GCAAATCAGCTG
CACAACGGAAACGCAATACAGTTGTGGCCATGCAAGTCTAATACAGATGCAAATCAGCTC
---------+---------+---------+---------+---------+---------+ 1080
GTGTTGCCTTTGCGTTATGTCAACACCGGTACGTTCAGATTATGTCTACGTTTAGTCGAG
3'                                                        GTCGTC
H  N  G  N  A  I  Q  L  W  P  C  K  S  N  T  D  A  N  Q  L  -
  30             35             40             45

TGGACTTTG oligonucleotide
TGGACTTTGAAAAGAGACAATACTATTCGATCTAATGGAAAGTGTTTAACTACTTACGGG
---------+---------+---------+---------+---------+---------+ 1140
ACCTGAAACTTTTCTCTGTTATGATAAGCTAGATTACCTTTCACAAATTGATGAATGCCC
W  T  L  K  R  D  N  T  I  R  S  N  G  K  C  L  T  T  Y  G  -
  50             55             60             65
```

FIG. 10a

```
                                     Xba 1
                                    (TCTAGA)
                             GGGTTGGTTCTAGATGTGAGGG
     GGAACCATTTTAAATTTGTATAGTGGGTTGGTGTTAGATGTGAGGGCATCGGATCCGAGC
1600 +---------+---------+---------+---------+---------+--------- 1659
     CCTTGGTAAAATTTAAACATATCACCCAACCACAATGTACACTCCCGTAGCCTAGGCTCG
                                     AGATCA
     G  T  I  L  N  L  Y  S  G  L  V  L  D  V  R  A  S  D  P  S  -
                                        234

                                                           CCA
     CTTAAACAAATCATTCTTTACCCTCTCCATGGTGACCCAAACCAAATATGGTTACCATTA
1660 +---------+---------+---------+---------+---------+--------- 1719
     GAATTTGTTTAGTAAGAAATGGGAGAGGTACCACTGGGTTTGGTTTATACCAATGGTAAT
     L  K  G  I  I  L  Y  P  L  H  G  D  P  N  G  I  W  L  P  L  -
                               251         255
               Sac 2
              (CCGCGG)
     TTTTGATAGACCGCGGACTCTCTTGCAG
     TTTTGATAGACAGATTACTCTCTTGCAGTGTGTATGTCCTGCCATGAAAATAGATGGCTT
1720 +---------+---------+---------+---------+---------+--------- 1779
     AAAACTATCTGTCTAATGAGAGAACGTCACACATACAGGACGGTACTTTTATCTACCGAA
     F  *  *  T  D  Y  S  L  A  V  C  M  S  C  H  E  N  R  W  L  -
```

FIG. 10b

RECOMBINANT RICIN TOXIN FRAGMENTS

CROSS REFERENCE TO RELATED APPLICATIONS

This is a continuation-in-part of copending U.S. Ser. No. 717,319 filed Mar. 29, 1985, which is a continuation-in-part of U.S. Ser. No. 578,121 filed Feb. 8, 1984, now abandoned.

DESCRIPTION

1. Technical Field

This invention relates to the production of toxin fragments using recombinant technology. More specifically, the invention relates to producing ricin toxin B fragment using recombinant means, and in particular relates to muteins of ricin B that have decreased binding to galactosides.

2. Background Art

Ricin toxin (RT or ricin) is a naturally occurring toxin composed of an enzymatically active, cytotoxic "A" amino acid sequence, and a "B" sequence, which is presumed to be responsible both for attaching the "A" sequence to a target cell to be killed, and to aid in the translocation or transport of A fragment into the cytoplasm. Other examples of such toxins include diphtheria toxin and the exotoxin from *Pseudomonas aeruginosa.* Other toxic proteins, such as, for example, those derived from *Phytolacca americana* (PAPI, PAPII, and PAP-S) and gelonin show in vitro activities comparable to the "A" sequences of the above toxins, but are much less active in vivo, presumably due to the absence of a "B" chain.

The "ricin" peptides of the present invention are derived from the seeds of *Ricinus communis* commonly known as castor beans. Two similar proteins (often called lectins) are extractable from these seeds: the above-mentioned ricin and *Ricin communis* agglutinin (RCA). Both proteins contain A and B portions; however, the A and B portions do not comprise a single peptide. The A portions or these moieties are capable of catalytically inactivating the large subunit of ribosomes in vitro and the mechanism of ricin for in vivo cytotoxicity is believed to reside in this capacity for ribosome inactivation. Ricin and RCA appear to be highly homologous (Cawley, D. B., et al, *Arch. Biochem. Biophys.* (1978) 190:744) but differences exist. RCA is dramatically less toxic, and appears to exhibit some characteristics corresponding to those expected of a dimer of ricin.

The components of ricin and of RCA have been well characterized and sequenced on the basis of the extracted materials (Funatsu, G., et al., *Agric. Biol. Chem.* (1979) 43:2221). Ricin has an apparent molecular weight of 58,000 daltons and consists of the A chain with a molecular weight of 32,000 daltons and a B chain of molecular weight of 34,700 daltons. RCA is a tetramer which has two A subunits of molecular weight 32,000, and two B subunits of molecular weight 36,000 each. In their native environments, the B chains are generally glycosylated. The A and B subunits of both ricin and RCA are linked only by a single disulfide bond, and not by peptide linkage (Funatsu, G., et al., *Agri. Biol. Chem.* (1977) 41:1211) unlike, for example, diphtheria toxin which is found as a single chain peptide. It is also known that both ricin and RCA, though having separate peptides for A and B portions, are derived from a single chain precursor in each case (Butterworth, H. E., et al. *Eur. J. Biochem.* (1983) 137:57). As a result of the work related to the present invention, it has been shown that the single chain precursor appears to contain a sequence of 12 amino acids between the A chain (amino terminal) and B chain sequence. It is assumed that upon excision of the dodecameric intervening peptide, the A and B chains remain linked through the single disulfide bond.

The present invention provides a means for obtaining the B chain of ricin using recombinant technology thus providing with greater accuracy the entire amino acid sequence, and making possible an exploration of the structural features required for its activity. The techniques and materials of the present invention further permit selective modification of the amino acid sequence of the B chain and thus permit manipulation to provide properties which are capable of enhancing the cytoxicity of ricin or of other toxins and the derivatives thereof. By enabling the production of ricin B chain using predictable, efficient, and economic procedures which, further, permit directed modification, the invention permits the use of B chain in practical and improved ways not before possible.

BRIEF DESCRIPTION OF THE INVENTION

The invention relates, in one respect, to ricin B which is prepared using recombinant techniques. The amino acid sequence of the ricin B can be, if desired, absolutely identical to the ricin B peptide amino acid sequence as extracted from castor bean seeds, but the recombinant product is inevitably somewhat modified due to the environment of its production, and may be further modified at the will of the producer to contain alterations in amino acid sequence or in the level of glycosylation. Accordingly, one aspect of the invention is a method of production of ricin B by recombinant techniques, and the ricin B so produced.

In other aspects, the invention is directed to expression vectors which are capable of effecting the expression of the ricin B chain, to host cells which have been transformed with such vectors, and to cultures thereof.

One aspect of the invention concerns muteins of ricin B in which at least one amino acid of at least one galactoside binding site of ricin B is altered to decrease or eliminate the binding of ricin B to galactosides.

In another aspect of the invention, at least one amino acid of those that are within 5 Angstroms of the galactoside in the 2A resolution crystal structure of ricin is altered by substitution or deletion, whereby the binding of galactoside to the ricin B chain is decreased.

In yet another aspect of the invention, at least one amino acid that participates in hydrogen bonding of the galactoside binding site to the galactoside is deleted or substituted.

In yet another aspect of the invention, at least one aromatic or heterocyclic amino acid that comprises part of the galactoside binding site of ricin B is deleted or substituted with a non-aromatic non-heterocyclic amino acid.

In still another aspect of the invention, at least one amino acid of the galactoside binding site is substituted by one which sterically hinders the bonding of galactoside by the galactoside binding site of ricin B.

In still yet another aspect of the invention at least one amino acid of the galactoside binding site is substituted by a cysteine residue, which is optionally derivatized with a reagent specific for thiol groups.

The invention also concerns muteins of ricin and ricin precursor comprising the ricin B muteins covalently joined to ricin A chain.

Also, aspects of the invention are DNA sequences encoding the ricin B muteins, ricin precursor and ricin which comprise the ricin B mutein, expression vectors comprising such DNA sequences operably linked to control sequences effective for expression of desired proteins in a recombinant host and host cells transformed with such expression vectors.

The invention also concerns conjugates comprising a binding moiety covalently bound to ricin wherein the ricin comprises a ricin B mutein.

A further aspect of the invention also concerns a method of use of ricin B muteins to enhance the cytotoxity of conjugates comprising a binding moiety wherein the binding moiety is conjugated to ricin toxin A or to ricin which comprises the ricin B mutein.

Also included in the invention is a method of treating a subject with a ricin B mutein alone or as a conjugate which may comprise ricin B mutein or ricin wherein the B chain thereof is ricin B mutein, and a method of treating a subject with a ricin toxin A conjugate and the ricin B mutein.

BRIEF DESCRIPTION OF THE DRAWINGS

FIG. 2 shows the protein sequence of ricin B as disclosed by Funatsu (supra) and obtained from the extracted protein.

FIG. 3 shows the nucleotide sequence of the cDNA insert of the plasmid pRTB5 corresponding to the ricin B chain partial coding sequence, along with the amino acid sequence deduced from it. Also shown for comparison is the sequence of ricin B as determined from the extracted protein by Funatsu.

FIG. 4A and 4B shows a comparison of base (4A) and protein (4B) sequence of the aforementioned cDNA insert with a cDNA insert of the plasmid pRTB4 which encodes a major portion of the sequence of the B portion of RCA. Also shown is the sequence of pRTA115, which overlaps a portion of the pRTB5 sequence.

FIG. 5A shows the sequences of the synthetic oligonucleotides used to complete the coding sequence of ricin B derived from pRTB5.

FIG. 5B shows the sequenced portion of pRTB236 representing the $\beta$-galactosidase/ricin B fusion.

FIG. 5C shows the sequenced portion of pRTB514 which contains the junction between the pDG141 ribosome biding site and the coding sequence from pRTB601.

FIG. 10A shows the position and sequence of oligodeoxyribonucleotide primers used to create SalI and PvuII sites in the amino terminal region of the ricin B sequence.

FIG. 10B shows the position and sequence of oligodeoxyribonucleotide primers used to create an XbaI and SacII site in the carboxyl terminal region of the ricin B sequence. The numbers at the right of the figures are nucleotide numbers in the complete ricin sequence. Amino acids are designated by the single letter observations approved by the IUPAC-IUB Commission on Biochemical Nomenclature.

MODES FOR CARRYING OUT THE INVENTION

A. Definitions

Figure 1:
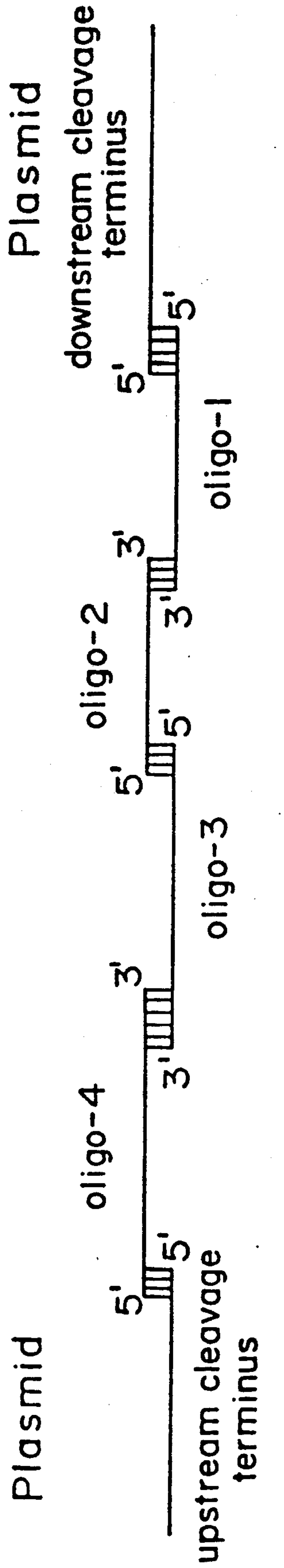
FIG. 1 is a diagramatic representation of the process for completing the coding sequence of an isolated cDNA using tandem single-stranded oligonucleotide bridges.

As used herein, "ricin B" refers to a protein whose amino acid sequence is substantially similar to that of the ricin B peptide which is extractable from castor bean seeds. The ricin B of castor beans is approximately 262 amino acids in length and has a molecular weight of approximately 34,700 daltons. However, it is known that the precise sequence varies depending on the variety of bean.

"Substantially similar" means that the protein in question must be approximately the same length of ricin B (arbitrarily within around 10%) but, more importantly, must retain the functional ability of ricin B chain to faciliate the intracellularization of an associated toxin molecule. It is well known that some small alterations in protein sequence may be possible without disturbing the functional abilities of the protein molecule, although other modifications are totally destructive. It is not currently possible to predict with any assurance into which category a particular alteration will fall. The definition herein permits any modifications which are in the first category. Such alterations could result from chance mutations in the gene sequence or from deliberate alterations thereof. Further, as is well known, protein sequences may be modified by association with other molecules such as glycosides, lipids, or inorganic ions such as phosphate. The ionization status will also vary depending on the pH of the medium or the pH at which crystallization or precipitation of the isolated form occurs. Further, the presence of air may cause oxidation of labile groups, such as —SH. Intended within the definition of ricin B are all such modifications of a particular primary structure, i.e., e.g., both glycosylated and non-glycosylated forms, neutral forms, acid and basic salts, lipid or other associated peptide forms, side chain alterations due to oxidation or derivatization, and any other such modifications of an amino acid sequence which would be encoded by the same genetic codon sequence.

"Ricin B muteins" according to the invention are substantially similar forms of ricin B according to the invention in that they fulfill the functional definition of facilitating the intracellularization of an associated toxin molecule. The alterations of the galactoside binding sites of the ricin B muteins decrease the affinity of the ricin B muteins according to the invention for galactosides, yet retain, at least partial functional ability to facilitate the intracellularization of an associated toxin molecule.

"Impurities" as used in describing ricin B prepared by the method of the invention refers to materials normally associated with ricin B as produced in the castor bean seeds, which are not included among the protein modifications above. Accordingly, "impurities" refers to ricin A and agglutinin as well as to the castor bean cellular materials which ordinarily are associated with ricin B nonspecifically.

"Recombinant host cells" refers to cells which have been transformed with DNA sequences constructed by recombinant techniques. Such reference includes both the cells as separated, for example by filtration or as a centrifugation pellet, and to cultures of these cells. Indeed, "cells" and "cell cultures," where the context so permits, are used interchangeably herein.

"Operably linked" refers to juxtaposition such that the normal function of the components can be performed. Thus, a coding sequence "operably linked" to control sequences refers to a configuration wherein the coding sequence can be expressed under the control of these sequences.

"Control sequences" refers to DNA sequences necessary for the expression of an operably linked coding sequence in a particular host organism. The control sequences which are suitable for procaryotes, for example, include a promoter, optionally an operator sequence, a ribosome binding site, and possibly, other as yet poorly understood sequences. Eucaryotic cells are known to utilize promoters, polyadenylation signals, and enhancers.

"Expression system" refers to DNA sequences containing a desired coding sequence and control sequences in operable linkage, so that hosts transformed with these sequences are capable of producing the encoded proteins. In order to effect transformation, the expression system may be included on a vector; however, the relevant DNA may then also be integrated into the host chromosome.

As used herein "cell", "cell line", and "cell culture" are used interchangeably and all such designations include progeny. Thus "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny which have the same functionality as screened for in the originally transformed cell, are included. Where distinct designations are intended, it will be clear from the context.

B. Muteins of Ricin B

Ricin B has two functional characteristics, it first plays a role in binding to galactoside on the surface of cells and then participates in the internalization of ricin toxin A chain into the cell. The muteins of ricin B according to the invention have amino acid sequences that are specifically altered from those described sequences herein for ricin toxin B chain. The alterations are made in amino acids that comprise the galactoside binding sites of ricin B, and most preferably in amino acids that affect the binding of ricin B chain to galactosides, e.g., lactose. The muteins of ricin B of the present invention are altered in these amino acids to decrease the binding of ricin B to galactoside.

B.1. IDENTIFICATION OF GALACTOSIDE BINDING SITES OF RICIN B

B.1.A. General Description of the Structure of Ricin B

Figure 9:
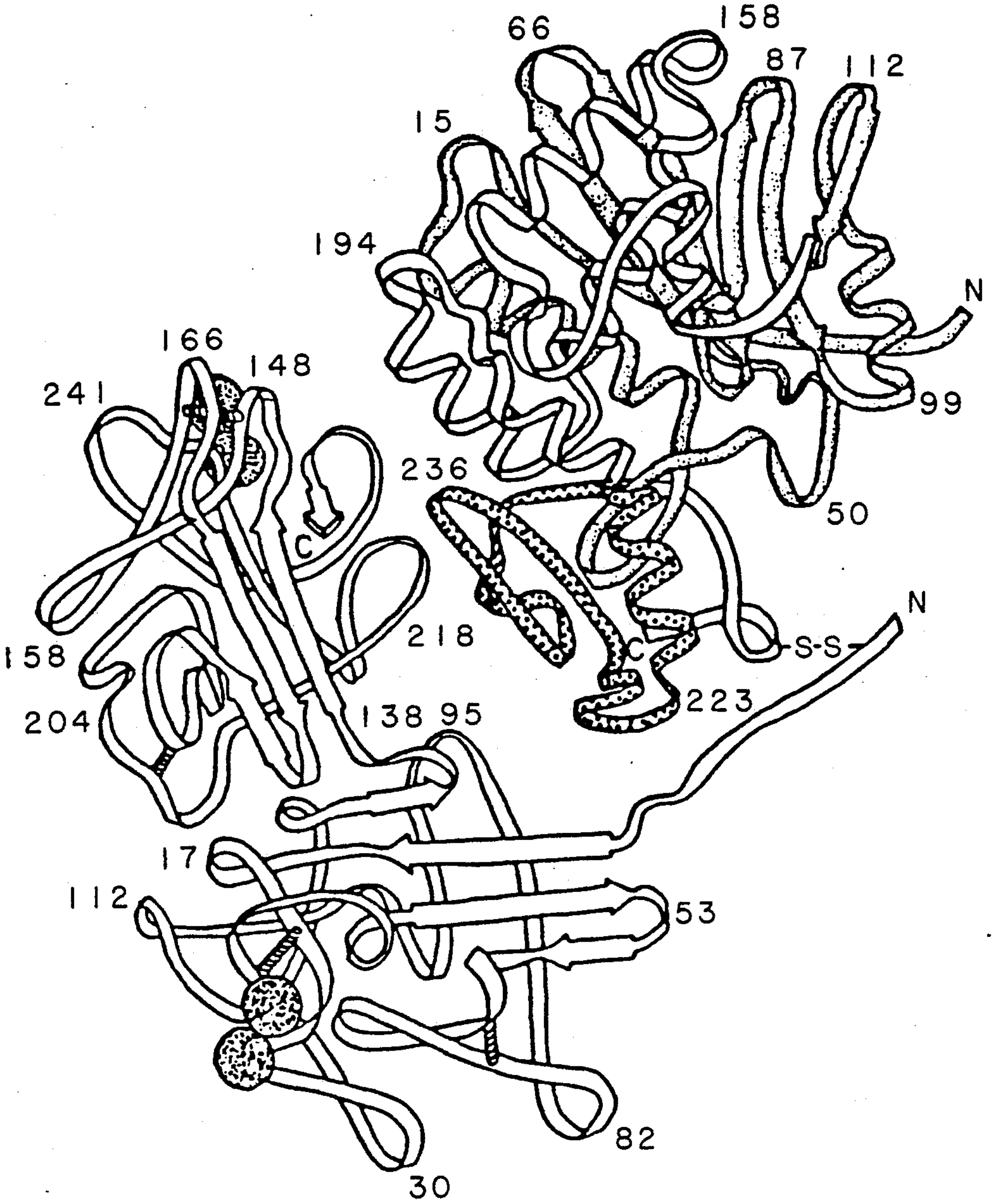
FIG. 9 is a ribbon representation of the ricin backbone. The A chain is in the upper right and the B chain at lower left. The two lactose moieties bound to the B chain are each represented as pairs of discs. The chains have been separated slightly to facilitate viewing. The disulfide bond linking the chains is indicated in the lower right portion of the molecule.

The three dimensional structure of the ricin B molecule has been determined to a resolution of 2.8 Angstroms Å by Robertus et al., and a two dimensional representation of the ricin B chain structure is shown in FIG. 9.

The representation shows two domains within each B chain of ricin and each domain has a galactoside binding region. Each domain of the ricin B chain has two of disulfide loops, and each domain has a single galactoside binding site. The two domains have folding patterns that are similar and can be classified for purposes of the invention as an amino terminal domain encompassing amino acid residues 1–135 which includes the amino galactoside binding site, and a carboxyl terminal domain encompassing amino acids 136–267 which includes the carboxyl galactoside binding site.

The amino galactoside binding site is defined by two amino acid sequences, residues 22–28 (Asn22, Va123, Arg24, Asp25, Gly26, Arg27, and Phe28) and residues 35–46 (Gln35 Leu36 Trp37 Pro38 Cys39 Lys40 Ser41 Asn42 Thr43, Asp44 Ala45 and Asn46). Amino acids that can potentially interact with galactose are contained within the residues 22–28 and 35–46. The carboxyl galactoside binding site may be defined by three amino acid sequences, residues 197–200 (Arg197, Glu198, Thr199 and Va1200) residues 233–239 (Leu233 Asp234 Va1235 Arg236 Ala238 Ser238 Asp239) and residues 244–256 (Gln244, Ile245, Ile246, Leu247, Tyr248, Pro249, Leu250, His251, Gly252, Asp253, Pro254, Asn255 and Gln256). Amino acids that can potentially interact with galactose are contained within the residues 233–239 and 244–256. Not all of the residues described above however are considered to bind to lactose.

A computer analysis of the 2.8 Angstrom (Å) crystallographic structure of the ricin B chain was carried out using Mogli protein modeling program on an Evans and Sutherland Graphics System both of which are commercially available from Evans and Sutherland, Salt Lake City, Utah, U.S.A. Table 1, generated using this system, shows the distances in Angstroms of particular amino acid residues of the amino galactoside binding site of ricin B to some part of the lactose residue bound therein.

TABLE 1

| Protein Residue | Residue Atom | Lactose Residue | Lactose Atom | Distance (Angstrom) |
|---|---|---|---|---|
| Trp37 | N | Gal | O6 | 5.95 |
| Trp37 | C6 | Gal | O6 | 4.47 |
| Trp37 | C7 | Gal | O2 | 6.67 |
| Arg27 | C5 | Gal | O6 | 8.56 |
| Phe28 | C4 | Gal | O6 | 10.9 |
| Pro38 | C6 | Gal | O6 | 8.93 |
| Val23 | C5 | Gal | O6 | 8.20 |
| Asn42 | O | Gal | O3 | 11.0 |
| Gln35 | N | Gal | O6 | 2.09 |
| Gln35 | O | Gal | O6 | 2.31 |
| Asn46 | N | Gal | O4 | 3.12 |
| Asn46 | O | Gal | O3 | 2.45 |
| Asn46 | N | Gal | O3 | 2.85 |
| Asp22 | O | Gal | O3 | 2.65 |
| Asp22 | O | Gal | O4 | 4.21 |
| Asp25 | O | Glc | O2 | 3.79 |
| Asp25 | O | Gal | O3 | 5.71 |
| Asp25 | C3 | Gal | O6 | 5.03 |
| Asp25 | O | Gal | O6 | 4.26 |
| Asp25 | O | Gal | O6 | 5.14 |
| Lys40 | N | Gal | O3 | 2.37 |
| Lys40 | N | Gal | O2 | 2.86 |
| Arg24 | C5 | Gal | O6 | 2.86 |
| Asp44 | O | Glc | C6 | 5.29 |
| Asp44 | O | Glc | O6 | 5.29 |

From these data, residues within 3 Angstroms of an atom in lactose are:
Asp22 Arg24 Asn46 Gln35 Lys40

Further analysis was carried out to determine the part of the structures of the amino acids of the amino galactoside binding site and lactose bound within the site that fall within specified distances of one another. The results of the analysis, in Table 2, showed that the indicated parts of the following amino acid side chains were within the specified distance of some part of galactose.

TABLE 2

| | Distance | | |
|---|---|---|---|
| Residue | 3Å | 4Å | 5Å |
| Asp22 | C—COO | C—COO | C—COO |
| Arg24 | C—C—C | C—C—C C=O | ALL SIDE CHAIN |
| Asp25 | C C=O | C—C—COO C=O | C—C—COO C=O |
| Gly26 | | | |
| Gln35 | C—CON | C—C—CON | C—C—CON |
| Lys40 | C—N | C—C—N | C—C—C—C—N |
| Asn46 | C—N | C—CON | C—CON |
| Trp37 | | C3-C8 C11 N | ALL SIDE CHAIN |
| Asp44 | | | COO |

The same computer analysis was carried out on the carboxyl galactoside binding site. Table 3 shows the distances of particular amino acids residues of the carboxyl galactoside binding site of ricin B to some part of the lactose residue bound therein.

TABLE 3

| Carboxyl Terminal Domain | | | | |
|---|---|---|---|---|
| Protein Residue | Atom | Lactose Residue | Atom | Distance- (Angstrom) |
| Tyr248 | O | Gal | O2 | 5.34 |
| Try248 | C6 | Gal | O2 | 6.42 |
| Tyr248 | C8 | Gal | O3 | 4.61 |
| Tyn248 | C5 | Gal | O3 | 6.43 |
| Arg236 | N | Glc | O2 | 8.09 |
| His251 | C6 | Gal | O3 | 2.97 |
| Asp234 | O | Gal | O4 | 3.21 |
| Asp234 | O | Gal | O4 | 3.30 |
| Asp255 | N | Gal | O4 | 2.58 |
| Asn255 | O | Gal | O4 | 3.74 |
| Asn255 | O | Gal | O3 | 4.06 |
| Asn255 | N | Gal | O3 | 4.39 |
| Ala237 | O | Gal | O3 | 3.51 |
| Ile246 | C6 | Gal | C6 | 2.94 |

From these data, residues within 3 Angstroms of an atom in lactose are:
Ile246 Asn255 His251

The same analysis used to generate the data in Table 2 showed that the indicated parts of the structure amino acid residues of the carboxyl galactoside binding site of Table 4 are within the specified distances of a part of galactose.

TABLE 4

| | Distance | | |
|---|---|---|---|
| Residue | 3Å | 4Å | 5Å |
| His251 | N—C—N | C—N—C—N—C | ALL SIDE CHAIN |
| Asn255 | C—N | C—C—N | ALL SIDE CHAIN |
| Arg236 | Ca—C | C—C—C C=O | C—C—C C=O |
| Ile246 | C—C | C—C C—C | C—C C—C |
| Asp234 | C—COO | C—COO | |
| Ala237 | C C=O | C C=O | |
| Gln256 | | C—N | |
| Tyr248 | C—C—C—C—C ALL SIDE CHAIN | | |

B.1.B ALTERATIONS IN AMINO ACIDS INVOLVED IN BONDING TO GALACTOSIDE

1. Alteration of Hydrogen Bonding Amino Acids

All of the amino acids in Tables 2 and 4 have proximities close enough to galactose to be involved in the binding of galactoside in the respective amino or the carboxy galactoside binding sites.

Asp22, Gln35, Lys40, and Asn46 all are within 3.25 A of at least one atom of galactose. The nature of the side groups of the amino acids and galactose that are within 3.75 A of one another suggest that they are hydrogen bonded. The approximate bond lengths of biologically important hydrogen bonds range from to $3.10 \pm 0.13$ A and below. (See *Molecular Biology of the Gene,* Watson ed., W. A. Benjamin Inc., New York, 2nd Edition (1970). A hydrogen bond can be considered to be an intermediate stage of transfer of a proton from an acid to a base. The strength of a hydrogen bond increases with the acidity (ability to donate a proton) of the proton donor and with the basicity (ability to accept a proton) of the proton acceptor. Hydrogen bonds can arise between covalently bound hydrogen atoms having a positive charge and negatively charged covalently bound, acceptor atoms, e.g., $C{=}0^-$, or between groups of atoms having a unit charge. By changing the charge of the side groups of the amino acids forming hydrogen bonds, or by chemical derivatization of the side group involved, or by substitution of the amino acid with a different amino acid that does not form a hydrogen bond, for example, one that has uncharged or oppositely charge side groups, or lastly, by deleting the amino acid involved in hydrogen bonding, the binding of galactoside by the galactose binding site is decreased.

Within the scope of the invention are alterations in amino acids that form hydrogen bonds with the galactoside. Such alterations include amino acid derivatives, amino acid substitutions and deletions that result in a decrease in binding of galactoside to the galactoside binding site or sites. Amino acid residues to which such alterations may be carried out are those that form hydrogen bonds with the galactoside, and amino acids stabilizing amino acids that form hydrogen bonds with the galactoside. With respect to the amino galactoside bonding site, residues Asp22, Arg24, Gln35, Lys40 and Asn46 of the ricin B chain are in positions that indicate potential formation of hydrogen bonds with galactoside. With respect to the carboxyl galactoside bonding site, residues His251 and Asn255 are in positions that indicate potential formation of hydrogen bonds with galactoside. Furthermore, Asp234 also is in a position that suggests hydrogen bond formation.

Amino acid residues that stabilize an amino acid which is in a position to form a hydrogen bond with galactoside are Asp22 of the amino galactoside binding site, and Asp234 of the carboxy galactoside binding site. Both of these residues may also participate in hydrogen bonding to the galactoside. Intervening water molecules between amino acid residues, such as Asn255, may hydrogen bond to galactose.

Muteins of ricin B according to the invention may be formed by deletion or substitution of at least one of the amino acids that form hydrogen bonds with galactoside or stabilize amino acids that form hydrogen bonds with galactoside. Such substituting amino acids that do not form hydrogen bonds will generally have either a side group that lacks charge, such as glycine, alanine, valine, isoleucine, leucine. Substituting amino acids with no side chain (glycine) or short side chain are generally preferred. Also preferred are amino acids having side chains that are oppositely charged from side chain of the amino acid for which it substitutes. Thus, when aspartic acid or glutamic acid are the residues in the native ricin B chain to be substituted, both of which have negatively charged carboxyl side groups, lysine and arginine, which have terminal amino side groups are preferred in the ricin B mutein. Conversely when lysine or arginine are the residues in the native ricin B chain to be replaced, aspartic or glutamic acid residues are used as replacements in the ricin B chain mutein. In general, it is preferred to replace hydrogen bonding or stabilizing amino acids with those having small uncharged side groups, such as glycine and alanine. Such amino acids are sufficiently small that binding of the galactoside through the weak interaction of Van der Waals forces is not expected.

The following Tables ≡and 6 show the substitutions for particular residues in decending order of preference. The most preferred are at the top of the list and the least preferred substitutions are at the bottom of the list. Amino acids in the middle of the list are placed only in approximate relative preference. Each substitution may be made singly independent of substitution of any of the other replaced amino acids. Multiple amino acids in the native sequence may be replaced.

TABLE 5

| | | Amino Galactoside Binding Site | | | | |
|---|---|---|---|---|---|---|
| Asp22 | Arg24 | Asp25 | Gln35 | Trp37 | Lys40 | Asn46 |
| Gly | Gly | Gly | Gly | Gly | Gly | Gly |
| Ala | Ala | Ala | Ala | Ala | Ala | Ala |
| Ser | Asp | Ser | Asp | Ser | Asp | Lys |
| Lys | Glu | Lys | Glu | Thr | Glu | Arg |
| Arg | Val | Arg | Asn | Asn | Val | Asp |
| Asn | Ser | Asn | Leu | Val | Ser | Glu |
| Glu | Thr | Glu | Ile | Gln | Thr | Gln |
| Gln | His | Gln | Val | Cys | His | Leu |
| Leu | Lys | Leu | Lys | Lys | Arg | Ile |
| Ile | Cys | Ile | Arg | Arg | Cys | Val |
| Val | Asn | Val | His | Asp | Asn | His |
| His | Gln | His | Ser | Glu | Gln | Ser |
| Thr | Leu | Thr | Thr | Ile | Leu | Thr |
| Met | Ile | Met | Met | Leu | Ile | Met |
| Cys | Met | Cys | Cys | Met | Met | Cys |
| Phe | Phe | Phe | Phe | His | Phe | Phe |
| Tyr | Tyr | Tyr | Tyr | Phe | Tyr | Tyr |
| Trp | Trp | Trp | Trp | Tyr | Trp | Trp |
| Pro | Pro | Pro | Pro | Pro | Pro | Pro |

TABLE 6

| | | Carboxyl Galactoside Binding Site | | | | |
|---|---|---|---|---|---|---|
| Asp234 | Arg236 | Ala237 | Ile246 | Tyr248 | His251 | Asn255 |
| Gly | Gly | Leu | Gly | Gly | Gly | Gly |
| Ala | Ala | Ile | Ala | Ala | Ala | Ala |
| Ser | Asp | Val | Ser | Ser | Asp | Lys |
| Lys | Glu | Lys | Thr | Thr | Glu | Arg |
| Arg | Lys | Arg | Val | Asp | Lys | Asp |
| Asn | His | Asp | Asn | Glu | Arg | Gln |
| Glu | Ser | Glu | Gln | Asn | Ser | Glu |
| Gln | Thr | Ser | Cys | Gln | Thr | Leu |
| Leu | Val | Thr | Lys | Val | Val | Ile |
| Ile | Leu | Asn | Arg | Ile | Leu | Val |
| Val | Ile | Gln | Asp | Leu | Ile | His |
| His | Phe | Cys | Glu | Lys | Phe | Ser |
| Thr | Tyr | Met | Ile | Arg | Tyr | Thr |
| Met | Gln | Gly | Leu | His | Gln | Met |
| Cys | Asn | His | Met | Met | Asn | Cys |
| Phe | Met | Phe | His | Cys | Met | Phe |
| Tyr | Cys | Tyr | Phe | Trp | Cys | Tyr |
| Trp | Trp | Trp | Tyr | Phe | Trp | Trp |
| Pro | Pro | Pro | Pro | Pro | Pro | Pro |

B.1.B.2 ALTERNATION OF AROMATIC AMINO ACIDS

Both the amino and carboxyl galactoside binding sites have one site that is formed by an aromatic amino acid residue, Trp37 and Tyr248 in the amino and carboxyl galactoside binding sites, respectively. The positioning of the aromatic side chain of these two amino acids in the respective galactoside binding site is substantially parallel to the ring of the lactose moiety in the 2.8 A resolution crystal structure of ricin B. As set out in Tables 2 and 4, the aromatic side chain of both of these amino acids is about 5 A from the lactose residue and substantial portions of each amino acid are within 4 A of the lactose residue. The distances of the side chains from the lactose ring are such that strong nonspecific attractive forces or Van der Waals interactions are indicated. Van der Waals interactions may occur over distances such as those indicated above between the aromatic ring of the amino acids and the ring structure of lactose.

In the muteins of ricin B, according to the invention, the aromatic amino acids are deleted or are substituted with amino acids that do not lead to stabilization of nonspecific attractive forces such as Van der Waals invention. In general, substitutions will be made with amino acids that do not have aromatic or heterocyclic side chains. Thus, substitution with tryptophan, phenylalanine, tyrosine and histidine are not desirable for either Trp37 or Tyr248. The substitutions are preferably made with amino acids that have small side chains. Most preferred are those that do not have significant charge separation and therefore do not have the potential for formation of stabilizing hydrogen bonds. Glycine and alanine are particularily preferred. Not desirable are large uncharged side chains such as those of leucine and isoleucine which, because of their extended uncharged structure, may have sufficient proximity to the lactose residue to stabilize the bonding thereto by Van der Waals interaction.

B.1.B.3. Double Alterations: Substitutions

Of course, combinations of substitutions at more than one residue of either or both galactoside binding sites are within the scope of the invention. To decrease binding to galactose by both the amino and carboxyl galactoside binding sites, it is preferable to alter at least one amino acid in each of the galactoside binding sites. Also within the scope of the invention are deletions of more than one residue of either or both galactoside binding site. Furthermore, combinations of at least one substitution and at least one deletion at amino acid residues of either or both galactoside binding site are within the scope of the invention.

The following Tables 7 and 8 list the preferred double substitutions in the amino and carboxy galactoside binding sites. Of course one or both galactoside binding sites may be double substituted or on galatoside binding site may be single substituted while the other is doubly substituted.

TABLE 7

| | Amino Galatoside Binding Site | | |
|---|---|---|---|
| Site 1 | Site 1 Substitution | Site 2 | Site 2 Substitution |
| Asp22 | Gly | Asn46 | Gly |
| Asp22 | Gly | Asn46 | Ala |
| Asp22 | Ala | Asn46 | Gly |
| Asp22 | Ala | Asn46 | Ala |
| Asp22 | Gly | Trp37 | Gly |
| Asp22 | Gly | Trp37 | Ala |
| Asp22 | Ala | Trp37 | Gly |
| Asp22 | Ala | Trp37 | Ala |
| Gln35 | Gly | Trp37 | Gly |
| Gln35 | Gly | Trp37 | Ala |
| Gln35 | Ala | Trp37 | Gly |

TABLE 7-continued

| | Amino Galatoside Binding Site | | |
|---|---|---|---|
| Site 1 | Site 1 Substitution | Site 2 | Site 2 Substitution |
| Gln35 | Ala | Trp37 | Ala |
| Asp22 | Gly | Asp25 | Gly |
| Asp22 | Gly | Asp25 | Ala |
| Asp22 | Ala | Asp25 | Gly |
| Asp22 | Ala | Asp25 | Ala |

TABLE 8

| | Carboxy Terminal Site | | |
|---|---|---|---|
| Site 1 | Site 1 Substitution | Site 2 | Site 2 Substitution |
| Asp234 | Gly | Asn255 | Gly |
| Asp234 | Gly | Asn255 | Ala |
| Asp234 | Ala | Asn255 | Gly |
| Asp234 | Ala | Asn255 | Ala |
| Asn255 | Gly | Tyr248 | Gly |
| Asn255 | Gly | Tyr248 | Ala |
| Asn255 | Ala | Tyr248 | Gly |
| Asn255 | Ala | Tyr248 | Ala |
| Asn255 | Gly | His251 | Gly |
| Asn255 | Gly | His251 | Ala |
| Asn255 | Ala | His251 | Gly |
| Asn255 | Ala | His251 | Ala |

The following Tables 9 and 10 indicate substitutions embodying modifications which increase the side chain size on one group and eliminate hydrogen bonding or Van der Waals interactions:

TABLE 9

| | Amino Terminal Site | | |
|---|---|---|---|
| Site 1 | Site 1 Substitution | Site 2 | Site 2 Substitution |
| Asp25 | Leu | Asn46 | Gly |
| Asn22 | Leu | Asn46 | Gly |

TABLE 10

| | Carboxyl Terminal Site: | | |
|---|---|---|---|
| Site 1 | Site 1 Substitution | Site 2 | Site 2 Substitution |
| Asp234 | Leu | Asn255 | Gly |

B.1.B.4 Substitutions with Cysteine

A cysteine residue or residue may be inserted into one or both of the galactoside binding sites of ricin B chain. The thiol group of cysteine reacts quickly under mild conditions with iodoacetate, iodoacetamide, N-ethylmaleimide and other reagents that are specific, or can be made specific, for thiol groups.

By replacing a side chain of an amino acid that contacts galactose in the binding site with cysteine, a site is provided for easy manipulation. After ricin B chain is folded, 8 thiol groups have formed 4 disulfide bonds. The ninth thiol group, Cys4, remains free. This can be either left and chemically modified, or it can be removed by site-specific modification (changed to a serine or other residue). If the molecule being modified is ricin, then Cys4 would be left and it would be linked to the interchain thiol group of ricin A chain to form a disulfide bond. In such a molecule the only thiol that can react with sulfhydryl reagents would be the cysteines inserted into the galactose binding pockets. The cysteine at 171 of ricin A chain has been shown to be unavailable for reaction as it is deeply situated in a hydrophobic region of the molecule.

The substitution of a cysteine residue for an amino acid in either or both of the galactoside binding sites may be sufficient to decrease or eliminate the binding of galactoside to ricin B. In addition to the extent that the binding of galactoside is not decreased by the abovementioned cysteine substitution, the cysteine residue may be derivatized with thiol specific groups such as alkylating agents to yield a cysteine derivative that interferes with galactoside binding.

The size of the thiol specific reagent may be increased if iodoacetamide, iodoacetate or N-ethylmaleimide did not prevent galactose binding. For example, the carboxyl group of iodoacetate may be linked in an amide bond to glycine. It could link to the amino group of cysteine in which the thiol group was blocked by a disulfide, such as with 5-thio-2-nitrobenzoic acid (TNB). After reaction with the recombinant ricin B chain, the thiol could be exposed by gentle reduction under conditions that did not reduce the disulfides on the protein. The thiol group could be modified with iodoacetate, iodoacetamide or N-ethylmaleimide. Various means for chemically derivatizing the cysteine residue placed in the galactoside binding site are possible and are considered within the scope of the invention to the extent that the ricin B mutein shows decreased binding to galactoside while retaining the ability to aid in translocation of the toxin molecule.

The following residues may be modified by substitution with cysteine:

| Amino terminal | Cartoxyl terminal |
|---|---|
| Asp 22 | Asp 234 |
| Arg 24 | Arg 246 |
| Asp 25 | Ala 237 |
| Gly 26 | Ile 246 |
| Gln 35 | Tyr 248 |
| Trp 37 | His 251 |
| Lys 40 | Asn 255 |
| Asn 46 | |

Asp 22 and Asn 46 for the amino galactoside binding site and Asp 234 and Asn 255 for the carboxyl galactoside binding site are the preferred residues for substitution with cysteine.

The nucleic acid and amino acid sequences in the amino terminal site are shown in FIG. 10A.

Residues 22 (Asp) and 46 (Asn) in the amino terminal site can be modified using the following oligonucleotides for site specific modification:

```
5'-CGAAATGGTCTATGTGTTTGCGTTAGGGATGGAAGATTCC-3'  Asp 22 to Cys
   CGAAATGGTCTATGTGTTGATGTTAGGGATGGAAGATTCC     ricin B sequence
   Arg Asn Gly Leu Cys Val Asp Val Arg Asp Gly Arg Phe His
                           22
```

-continued

```
5'-TGCAAGTCTAATACAGATGCAAATTGCCTCTGGCCATGCAAGTCT-3'   Gln 46 to Cys
   TGCAAGTCTAATACAGATGCAAATCAGCTCTGGCCATGCAAGTCT       ricin B sequence
   Cys Lys Ser AsanThr Asp Ala Asn Gln Leu Trp Pro Cys Lys Ser
                                46
```

The nucleic acid and amino acid sequence of the carboxyl terminal site are shown in FIG. 10B.

Amino acids 234 (Asp) and 255 (Asn) in the carboxyl galactoside binding sites can be modified using the following oligonucleotides:

```
5'-GTGGGTTGGTGTTATGCGTGAGGGCATCGGATCC-3'   Asp234 to Cys
   GTGGGTTGGTGTTAGATGTGAGGGCATCGGATCC       ricin B sequence
   G   L   V   L   D   V   R   A   S   D   P
                  234

5'-CCTCTCCATGGTGACCCATGCCAAATATGGTTACC-3'   Asn255 to Cys
   CCTCTCCATGGTGACCCAAACCAAATATGGTTACC       ricin B sequence
   P   L   H   G   D   P   N   Q   I   W   L   P
                         255
```

C. Methods for Carrying out Alterations of the Amino and Carboxy

Galactoside Binding Sites of Ricin B

A number of known methods may be used to carry out the desired modifications to form the ricin B muteins according to the invention.

Ricin B protein having the desired amino acid replacement or deletion may be made by conventional Merrifield synthesis as is known in the art. However, Merrifield synthesis of a complete ricin B molecule is undesirably complicated.

Substitutions and deletions may be accomplished by digesting to completion DNA encoding the native ricin B protein with specified endonucleases that cut in the region of the DNA surrounding the amino acid to be altered, removing the DNA fragment which encodes the amino acid residue or residues of the native ricin B galactoside binding site to be altered, and ligating, either under blunt ended or sticky ended conditions as appropriate, a double stranded DNA made of complementary chemically synthesized oligonucleotides that encode the desired amino acid alteration. The means for making such oligonucleotides are known and include commercially available automated DNA synthesizers such as that made by Biosearch, San Rafael, Calif.

Site-specific mutagenesis may also be used to carry out alterations to the DNA encoding specific amino acid. In general, the DNA encoding ricin B chain in the region to be altered is cut using an appropriate endonuclease, the fragment carrying the specific ricin region is removed, ligated into an appropriate vector such as an M13 vector and is mutagenized using a single-stranded oligodeoxyribonucleotide primer synthesized to insert, change, or delete nucleotides from the fragment after replication with an appropriate DNA polymerase.

To obtain the DNA fragment encoding the desired ricin B region, endonuclease restriction sites that are found in the native ricin B chain sequence may be used, or unique restriction sites on either side of the areas of interest are made in the DNA sequence of ricin B.

In a preferred embodiment, a new site for cleavage by SalI in the area of the amino galactoside binding site is made using site-specific mutagenesis to modify the sequence at Val21 and Asp22. Another site is created for cleavage by PvuII using the same technique to modify the base sequences around Gln47 and Leu48. Both modifications may be made without changing the amino acid sequence of ricin B. FIG. 10A illustrates the position of the SalI and PvuII sites that can be created and the oligonucleotide sequences that can be used to mutagenize the sequence of ricin B and retain the amino acid sequence.

Also in a preferred embodiment, a new site for cleavage by XbaI in the area of the carboxyl galactoside binding site is constructed by site-specific mutagenesis by modifying the sequence at Val232, Leu233 and Asp234. Another unique site is created for cleavage downstream of the carboxyl terminal galactoside binding site of the ricin B chain by SacII. FIG. 10B illustrates the position of the XbaI and SacII sites, and the oligonucleotide sequences that are used to mutagenize the sequence of ricin B and retain the amino acid sequence.

The unique restriction sites introduced into the ricin B sequence are produced by site-specific mutagenesis using conventional means. The above mentioned restriction sites are preferred because they do not alter the amino acid sequence of ricin B. Other unique restriction sites may be introduced as long as the amino acid sequence of ricin B is not changed, or if changed, the new sequence does not affect the essential biological properties of ricin B that relate to translocation.

As mentioned above, various methods may be used to introduce changes in the DNA sequence encoding amino acids of the amino terminal and carboxyl terminal galactoside binding sites. Double stranded oligodeoxyribonucleotides having "sticky ends" compatable with the unique restriction site engineered into the ricin B sequence by site-specific mutagenesis may be used. Such oligonucleotides may be made by conventional commercially available oligonucleotide synthesizers.

Table 11 shows the double-stranded oligodeoxyribonucleotide spanning the unique SalI to PvuII site engineered into the amino terminal region of the ricin B chain that encompasses the amino galactoside binding site. Table 12 shows the double-stranded oligodeoxyribonucleotide spanning the unique XbaI to SacII sites in the carboxyl region of ricin B chain that encompasses the carboxyl galactoside binding site. Each table shows the nucleotide changes required for the substitution of various amino acids. As mentioned above, the nucleotide change may be made to single or multiple amino acids in this region of the ricin B molecule. In addition, any of the changes may be made independently of all other changes.

TABLE 11

| Amino Acid # 22 | 35 | 37 | 40 | 46 |
|---|---|---|---|---|
| Asp | Gln | Trp | Lys | Asn |
| | Gly | Gly | Gly | Gly |
| | Ala | Ala | Ala | Ala |
| | Asp | Ser | Leu | Asp |
| | Glu | Thr | Ile | Gln |
| | Asn | Val | Asp | Gln |
| | | | | Leu |

22 35 37 40 46

TCGACGTTAGGGATGGAAGATTCCACAACGGAAACGCAATACGCAATA CAGTTGTGGCCATGCAAGTCTAATACAGATGCAAATCAG

ACAATCCCTACCTTCTAAGGTGTTGCCTTTGCGTTATGCGTTAT GTCAACACCGGTACGTTCAGATTATGTCTACGTTTAGTC

| 35 | 37 | 40 | 46 |
|---|---|---|---|
| GGG | GGT | GGC | GGT |
| CCC | CCA | CCG | CCA |
| GCG | GCG | GCG | GCG |
| CGC | CGC | CGC | CGC |
| GAT | TCC | CTG | GAT |
| CTA | AGG | GAC | CTA |
| GAA | ACC | ATC | GAA |
| CTT | TGG | TAG | CTT |
| AAC | GTG | GAT | CAG |
| TTG | CAC | CTA | GTC |
| | | | CTG |
| | | | GAC |

TABLE 12

| Amino Acid # 234 | 248 | 251 | 255 |
|---|---|---|---|
| Asp | Tyr | His | Asn |
| Gly | Gly | Gly | Gly |
| Ala | Ala | Ala | Ala |
| Gly | Ser | Asp | Glu |
| | | Glu | Gln |
| | | Lys | Asp |

234 248 251 255

CTAGATGTGAGGGCATCGGATCCGAGCCTTAAACAAATCATTCTT TACCCTCTCCATGGTGACCCAAACCAAATATGGTTACCATTATTTTGATAGACCGC

TACACTCCCGTAGCCTAGGCTCGGAATTTGTTTAGTAAGAA ATGGGAGAGGTACCACTGGGTTTGGTTTATACCAATGGTAATAAAACTATCTGG

| 234 | 248 | 251 | 255 |
|---|---|---|---|
| GGT | GGT | GGT | GGT |
| CA | CCA | CCA | CCA |
| GCG | GCG | GCG | GCG |
| GC | CGC | CGC | CGC |
| GAA | TCC | GAT | GAA |
| TT | AGG | CTA | CTT |
| | | GAA | CAG |
| | | CTT | GTC |
| | | AAA | GAT |
| | | TTT | CTA |

Deletions of amino acids may be made using essentially the same method, however, instead of changing the nucleotide sequence to encode a substituted amino acid, the complete trinucleotide codon encoding the amino acid to be deleted is removed. Such deletions are particularly desirable if they do not change the comformation of the protein, though not necessarily preferred for Trp37 and Tyr248.

Modifications of the DNA sequence encoding Asp22 may be made using the double-stranded break and repair method of Mandecki, Proc. *Natl. Acad. Sci.* USA 87:7177-7181 (1986).

Briefly, SalI cleaves the sequence 5'GTCGAC-3' at a position immediately 3' of the 5' G of this sequence, and the GAC portion codes for Asp22 in ricin B chain. Briefly, the plasmid comprising the ricin B sequence is cleaved at the SalI site, inserted as described above, to convert the circular structure to a linear one. An oligonucleotide containing sequences at either end that are identical to the ricin B chain DNA sequence with the site at residue 22 mutated to the desired amino acid is mixed with the linear plasmid. After heating and annealing, the DNA is used to transform cells rendered competent by calcium chloride treatment and incubation on ice followed by incubation at 37C for a short time. Transformed cells containing the desired mutation are then detected by using 32P-labelled oligonucleotide probes.

The sequence flanking and including the SalI site is as follows (the gap is to illustrate the SalI site):

```
                                          SalI cleavage site
                                            Asp22
5'
 CCCATAGTGCGTATCGTAGGTCGAAATGGTCTATGTG    TCGACGTTAGGGATGGAA
 GGGTATCACGCATAGCATCCAGCTTTACCAGATACACAGCT     GCAATCCCTACCTT
3'

                                                                  3'
GATTCCACAACGGAAACGCAATACAGTTGTGGCCATGCAAGTCTAATACAGATGCAAATCAG
CTAAGGTGTTGCCTTTGCGTTATGTCAACACCGGTACGTTCAGATTATGTCTACGTTTAGTC
                                                                  5'
```

The oligonucleotides to be used to repair the strand break and insert new amino acids substituting for Asp22 are shown in Table 13.

Modifications to the DNA sequence of the carboxyl galactoside binding site encoding Asp234 are made in essentially the same manner as described for the modifications of Asn22.

The sequence flanking and including the XbaII site is as follows (the ga is to illustrate the XbaI site):

```
                                        XbaI cleavage site
5'
GGAACCATTTTAAATTTGTATAGTGGGTTGGTT       CTAGATGTGAGGGCATCGGATCCG
CCTTGGTAAAATTTAAACATATCACCCAACCAAGATC       TACACTCCGGTAGCCTAGGC
3'

                                                      3'
AGCCTTAAACAAATCATTCTTTACCCTCTCCATGGTGACCCAAACCAAATATG
TCGGAATTTGTTTAGTAAGAAATGGGAGAGGTACCACTGGGTTTGGTTTATAC
                                                      5'
```

Gly, Ala and Glu codons are accomodated with retention of the XbaI restriction sequence as shown above in connection with Table 13. The repair oligonucleotides to introduce codons for amino acids that change the XbaI restriction sequence for Gln and Asn are shown in Table 14.

TABLE 13

| Amino Acid # | |
|---|---|
| 22 | 22 |
| Asp | GCGTATCGTAGGTCGAAATGGTCTATGTGTCGACGTTAGGGATGGAAGATTCGACAACAACGG |
| Gly | GGT |
| Ala | GCG |
| Asn | AAC |
| Glu | GAA |
| Gln | CAG |

TABLE 14

| Amino Acid # | |
|---|---|
| 234 | 234 |
| Asp | CCATTTTAAATTTGTATAGTGGGTTGGTTCTAGATGTGAGGGCATCGGATCCGAGCC |
| Gln | CAG |
| Asn | AAC |

In general, cloning and expression vectors used in conjunction with the ricin B sequence into which the unique restriction sites have been introduced, will lack the unique restriction sites. If necessary, restriction sites in the vector that are the same as the unique restriction sites may be removed by site-specific mutagenesis as is known in the art.

D. Vectors and Host Cells

The specific embodiments described hereinbelow set for procedures for constructing vectors compatible with procaryotes, and for transformation of such vectors into these host cells. *E. coli* K12 strain MM294 and a lambda lysogen of *E. coli* strain MC1000, are described in particular. However, other microbial strains may also be used, such as bacilli, for example *Bacillus subtilis,* various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived form an *E. coli* species by Bolivar, et al., *Gene* (1977) 2:95. pBR322 contains genes for ampicillin and tetracycline resistance, and thus provides markers which can be either retained or destroyed in constructing the desired vector. Commonly used procaryotic control sequences which are defined herein to include transcription initiation, an optional operator, and ribosome binding site sequences, include such commonly used promoters as the beta-lactamase (penicillinase) and lactose (lac) promoter systems (Chang, et al., *Nature* (1977) 198:1056) and the tryptophan (trp) promoter system (Goeddel, et al., *Nucleic Acids Res.* (1980) 8:4057) and the lambda derived $P_L$ promoter and N-gene ribosome binding site (Shimatake, et al., *Nature* (1981) 292:128) which has been made useful as a portable control cassette as set forth in U.S. Ser. No. 578,133 filed Feb. 8, 1984, now abandoned. However, any available promoter system compatible with procaryotes can be used.

In addition to bacteria, eucaryotic microbes, such as yeast, may also be used. *Saccharomyces cerevisiae,* Baker's yeast, is most commonly used although a number of other strains are commonly available. While vectors employing the 2 micron origin of replication are illustrated, Broach, J. R., *Meth. Enz.* (1983) 101:307, other plasmid vectors suitable for yeast expression are known (see, for example, Stinchcomb, et al., *Nature* (1979) 282:39, Tschempe, et al., *Gene* (1980) 10:157 and Clarke, L., et al., *Meth. Enz.* (1983) 1010:300). Control sequences for yeast vectors include promoters for the synthesis of glycolytic enzymes (Hess, et al., *J. Adv. Enzyme Reg.* (1968) 7:149; Holland, et al., *Biochemistry* (1978) 17:4900). Additional promoters known in the art include the promoter for 3-phosphoglycerate kinase (Hitzeman, et al., *J. Biol. Chem.* (1980) 255:2073), and those for other glycolytic enzymes, such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization (Holland, ibid). It is also believed terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid pEN046 (Holland, M. J., et al., *J. Biol. Chem.* (1981) 256:1385) or the LEU2 gene obtained from YEp13 (Broach, J., et al., *Gene* (1978) 18:121), however any vector containing a yeast compatible promoter, origin of replication and other control sequences is suitable. Secretion may also be accomplished in yeast using secretion sequences from Aspergillus glucoamylases, see, e.g., Innis et al., *Science* (1985) 228:21.

It is also, of course, possible to express the genes for the ricin B chain muteins in eucaryotic host cell cultures derived from multicellular organisms. See, for example, *Tissue Culture,* Academic Press, Cruz and Patterson, editors (1973). Useful host cell lines include the murine myelomas NS1, VERO and HeLa cells, Chinese hamster ovary (CHO) cells, COS-7 and its derivatives and CV-1 cells. Expression vectors for such cells ordinarily include promoters and control sequences compatible with mammalian cells such as, for example, the commonly used early and late promoters from Simian Virus 40 (SV40) (Fliers, et al., *Nature* (1978) 273:113 and Reddy et al., *Science* (1978) 200:494), or other viral promoters such as those derived from polyoma, Adenovirus 2, bovine papilloma virus, or avian sarcoma viruses, or immunoglobulin promoters and heat shock promoters. General aspects of mammalian cell host system transformations have been described by Axel, U.S. Pat. No. 4,399,216 issued Aug. 16, 1983. It now appears, also that "enhancer" regions are important in optimizing expression; these are, generally, sequences found upstream of the promoter region. Origins of replication may be obtained, if needed, from viral sources. However, integration into the chromosome is a common mechanism for DNA replication in eucaryotes. Plant cells are also now available as hosts, and control sequences compatible with plant cells such as the nopaline synthase promoter and polyadenylation signal sequences (Depicker, A., et al., *J. Mol. Appl. Gen.* (1982) 1:561) are available.

The successful expression attained by the invention depends upon correct utilization of the suitable control sequences to regulate expression of the desired toxin fragment. Therefore, whatever the host, control sequences compatible with and suitable for that host are positioned operably with respect to the coding sequence, using a properly placed "start" codon at the 5' end of the desired sequence. Any "native" control sequences are eliminated. The vectors of the invention place the coding sequence for the desired ricin B peptide fragments, immediately preceded by an ATG start codon directly downstream from control systems chosen to be compatible with the particular host.

It is also important, in obtaining good production of the desired fragments, to regulate the "time" of production so as to minimize any lethal effect on the host cell. Most typically, this is done by delaying expression of the ricin B sequences until substantial growth has occurred. Accordingly, it is desirable to utilize control sequences which are subject to environmental conditions. By maintaining conditions that repress expression during growth phase, and then converting to conditions which permit expression at the desired time, the negative aspects of any potentially lethal effect can be minimized.

In two particular preferred approaches, these regulatable control sequences are compatible with procaryotic hosts. The trp promoter is a regulatable promoter where expression of the operably linked sequence can be controlled by the level of tryptophan in the medium. By maintaining high tryptophan levels during growth, expression is repressed. Depletion or competitive inhibition of tryptophan turns on the promoter and permits expression.

Still more preferred is the $P_L$ promoter derived from $\lambda$ phage. This promoter is regulated by a protein which can be temperature sensitive. (There are mutant forms of the wild type repressor, e.g., cI857 which have this characteristic known in the art.) When used in a host which is able to synthesize this mutant form of repressor (such as *E. coli* K12 strain MC1000 lysogenic for the λ phage $N_7N_{53}cI_{857}SusP_{80}$), the $P_L$ promoter will be switched on when the temperature is raised because the higher temperature inactivates the mutant cI repressor. Thus, the host cells can be grown at low temperature without production of the foreign protein. The temperature is then raised when growth has been attained and ricin B production is desired.

Another, not necessarily independent approach, involves use of a plasmid which has temperature sensitive copy number control, so that if the cells are grown at low temperatures, coding sequences contained in the plasmid are replicated at low levels; at higher temperatures, the number of such copies is increased. The amount of protein produced is thus indirectly managed by regulating the number of available copies of its coding sequence.

If both approaches are used concomitantly, an increase in temperature results in both an increase in copy number and a derepression of promoter leading to substantial synthesis of otherwise repressed gene products.

E. Methods Employed

Vector construction employs ligation and restriction techniques known in the art. The quantity of DNA available can be increased by cloning the desired fragments, i.e., inserting into a suitable cloning vehicle, such as pBR322, pUC13 or pUC8, or γ charon vectors transforming and replicating in *E. coli,* and, optionally further enhancing through chloramphenicol amplification or by phage replication. The desired fragments can then be removed from the cloning vectors or phage and ligated to suitable promoters compatible with the host intended to be employed in the expression of the gene. Such hosts are then transformed with these expression vectors and cultured under conditions which favor stabilization of the plasmid and the safe production of the desired toxin fragments. Such conditions might include repression of the controlling promoter until most of logarithmic growth phase has been completed, and then altering conditions so as to favor the synthesis of the peptide. When the peptide has been synthesized, the cells are lysed, and the desired peptide or product recovered from the lysate.

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site-specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 μg of plasmid or DNA sequence is cleaved by one unit of enzyme in about 20 μl of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform followed by ether extraction and the nucleic acid is recovered from aqueous fractions by precipitation with ethanol followed by passage through a Sephadex G-50 spin column. If desired, size separation of the cleaved fragments may be performed by polyacrylamide gel electrophoresis using standard techniques. A general description of size separations is found in *Methods in Enzymology* (1980) 65:499-560.

Restriction cleaved fragments may be blunt ended by treating with the large fragment of *E. coli* DNA polymerase I (Klenow) in the presence of the four nucleotide triphosphates (dNTPs) using incubation times of about 15 to 25 minutes at 20° to 25° C. in 50 mM Tris pH 7.6, 50 mM NaCl, 6 mM $MgCl_2$. 6 mM DTT and 0.1 mM dNTPs. The Klenow fragment fills in at 5′ sticky ends but chews back single strands, even though the four dNTPs are present, at 3′ sticky ends. If desired, selective repair can be performed by supplying only one of the, or selected, dNTPs within the limitations dictated by the nature of the sticky ends. After treatment with Klenow, the mixture is extracted with phenol/-chloroform and ethanol precipitated followed by passage through a Sephadex G-50 spin column.

Two other nuclease enzymes are used in the procedures set forth below: Sl nuclease and exonuclease III.

Treatment with Sl nuclease under appropriate conditions results in rapid hydrolysis of any single-stranded portion of DNA and slow hydrolysis of double-stranded portions commencing at the ends. Sl nuclease hydrolyses are conducted in a buffer which is 15 mM sodium acetate, pH 4.5, 200 mM NaCl, and 1 mM $ZnSO_4$, using approximately 200 units per μl of Sl exonuclease 111. Ordinarily, 5000 units of Sl nuclease is used to hydrolyze approximately 10 μg of DNA.

Exonuclease III attacks double-stranded DNA, but hydrolyzes beginning at the 3′ end of the nucleotide sequence. Thus, digestion of a double-stranded DNA results in two 5′ protruding sticky ends. Hydrolysis is carried out in a buffer containing 15 mM Tris, pH 8, 10 mM NaCl, 1 mM $MgCl_2$, and 0.1 mM DTT, using approximately 2000 units per μl exonuclease 111. Ordinarily, 150 units of exonuclease III were used to react with 10 μg DNA.

Synthetic oligonucleotides are prepared by the triester method of Matteucci, et al., *J. Am. Chem. Soc.* (1981) 103:3185-3191) or by using commercially available synthesis. Kinasing of single strands prior to annealing or for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, 1-2 mM ATP. When using an oligonucleotide as a probe, 1.7 pmoles $\gamma^{32}P$ ATP (2.9 mCi/mmole), 0.1 mM spermidine, 0.1 mM EDTA may be used.

Ligations are formed using approximately equimolar amounts of the desired DNA fragments (2-10× excess of linkers or small oligomers) suitably end tailored to provide correct matching, by treatment with an excess, i.e., in a typical 15-30 μl reaction 0.4-4 Weiss units T4 DNA ligase and, when blunt-ended ligation is involved, 0.4-1 units of RNA ligase. Ligation mixtures are buffered at approximately pH 7.6 using 66 mM Tris along with 5 mM magnesium ion, 5 mM dithiothreitol, 1 mM ATP, and 0.1 mg/ml BSA for either blunt-end or sticky end ligations. Incubations are carried out at approximately 14 to 25° C. overnight.

In vector construction employing "vector fragments," the vector fragment is sometimes treated with bacterial alkaline phosphatase (BAP) in order to remove the 5' phosphate and prevent religation of the vector. BAP digestions are conducted at pH 8.3 in approximately 50 mM Tris, in the presence of $Mg^{+2}$ using about 1 unit of BAP per $\mu$l of vector at 60° C. for about one hour. In order to recover the nucleic acid fragments, the preparation is extracted with phenol/chloroform and ethanol precipitated and desalted by application to a Sephadex G-50 spin column. Alternatively, religation can be prevented in vectors which have been double digested by additional restriction enzyme cleavage of the unwanted fragments.

In the constructions set forth below, correct ligations for plasmid construction are confirmed by transforming *E. coli* strain MM294 obtained from *E. coli* Genetic Stock Center, CGSC #6135, or other suitable hosts with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al., *Proc. Natl. Acad. Sci.* (1969) 62:1159, following chloramphenicol amplification (Clewell, D. B., *J. Bacteriol.* (1972) 110:667) and analyzed by restriction and/or sequenced by the method of Messing, et al., *Nucleic Acids Res.* (1981) 9:309, or by the method of Maxam, et al., *Methods in Enzymology* (1980) 65:499.

G. Transformations

Depending on the host cell used, transformation is done using standard techniques appropriate to such cells. The calcium treatment employing calcium chloride, as described by Cohen, S. N., *Proc. Natl. Acad. Sci.* (USA) (1972) 69:2110 is used for procaryotes or other cells which contain substantial cell wall barriers. Infection with *Agrobacterium tumefaciens* (Shaw, C. H., et al., *Gene* (1983) 23:315) is used for certain plant cells. For mammalian cells without such cell walls, the calcium phosphate precipitation method of Graham and van der Eb, *Virology* (1978) 52:546 is preferred. Transformations into yeast are carried out according to the method of Van Solingen, P., et al., *J. Bact.* (1977) 130:946 and Hsiae, C. L., et al., *Proc. Natl. Acad. Sci.* (USA) (1979) 76:3829.

The host strains used in cloning and expression of the plasmids and set forth below:

For cloning and sequencing, in particular, *E. coli* strain MM294 (supra), Talmadge, K., et al., *Gene* (1980) 12:235; Meselson, J., et al., *Nature* (1968) 217:1110, was used as the host. However, when expression is under control of the $P_L$ promoter and $N_{RBS}$ the *E. coli* strain MC1000 Lambda $N_7N_{53}cI_{857}SusP_{80}$ as an expression host was used (ATCC 39531 deposited Dec. 21, 1983. This strain is hereinafter referred to as MC1000-39531.). This strain contains a lambda prophage which codes for a temperature sensitive $c_I$ repressor, which at the permissive temperature (30°-32° C.) is active. However, at the non-permissive temperature (36°-48° C.), the repressor is inactive and transcription from the $P_L$ promoter can proceed. It is further characteristic of this strain that at elevated temperatures the prophage fails to induce.

EXAMPLES

The following examples illustrate the invention by describing the production of expression vectors suitable for production of ricin B fragment in procaryotes. However, the ricin B and ricin B mutein of the invention can be ligated into a variety of vectors suitable for a range of other hosts.

H.1. Formation of a cDNA Library

The polyA mRNA prepared as in the parent copending application, U.S. Ser. No. 717,319, was used to obtain a cDNA library according to the method of Maniatis, et al. (supra). Briefly, a portion of the polyA RNA is treated under appropriate buffer conditions with reverse transcriptase and then treated with base to remaining mRNA. The resulting single-stranded cDNA is repaired using *E. coli* polymerase I (Klenow fragment) in the presence of the 4 dNTPs and the resulting "hairpin" then ligated using T4 ligase to a SalI linker (obtained from New England BioLabs). After treating the S1 nuclease and repairing with Klenow, the blunt end was ligated to an EcoRI linker using T4 ligase. After then digesting with EcoRI and SalI, the resulting double-stranded cDNA fragments, which are bounded by EcoRI and SalI restriction sites, were ligated into a EcoRI/SalI digested, BAP treated preparation of pUC13 obtained and freely available from J. Messing, the University of Minnesota. pUC13 is a modification of pBR322 capable of confering Amp resistance ($Amp^R$), which contains linkers bearing convenient restriction sites, including a PstI site downstream from the SalI site used in the insertion. pUC13 may also be regenerated from plasmid pUC303 which is available from the American Type Culture Collection under accession number 37247, see ATCC catalogue, 16th edition 1985. The resulting ligation mixture was used to transform *E. coli* MM294, and $Amp^R$ strains selected.

Successful transformants were transferred onto nitrocellulose membranes, and probed using the procedure of Grunstein & Hogness (supra), with the mixture of 16 synthetic oligonucleotides

5' CC(A)TC(A)TT(C)TT(A)AACATCC 3'
      G    G    T    G which was kinased with $^{32}P$. This mixture represents the anti-sense strand complementary to the codons for the amino acid sequence Trp-Met-Phe-Lys-Asn-Asp-Gly. Of about 5000 colonies probed, about 1% were found which hybridized to the probe. Plasmids were isolated from several representations of these colonies, and analyzed by restriction analysis and Maxam-Gilbert sequencing. Three plasmids, pRTB4, pRTB5, and pRTA115 were sequenced in the insert region.

FIGS. 3 and 4 show the results of this sequencing. FIG. 3 shows the sequence of the insert in pRTB5. Line 1 in FIG. 3 represents the amino acid sequence of ricin B as determined by Funatsu (supra). The second line represents the amino acid sequence deduced from the pRTB5 base sequence. An examination of the deduced sequence shows a high level of correspondence, although some discrepancies exist. These are due to errors in the published sequence and to varietal differences in the ricin B proteins represented. Line 3 is the base sequence of the isolated cDNA. The entire coding sequence for ricin B is present except for codons for the first 11 amino acids. (The lower case codons at the 5' end represent the EcoRI linker used as the source of the bulk of the coding sequence in the expression vectors.)

FIG. 4 shows a comparison of the sequences in pRTB4 and pRTB5. It is believed that the pRTB4 sequence represents the coding for RCA B chain. FIG. 4 also shows the overlap between pRTAI15 and pRTB5 which indicates that the RTA115 insert contains the upstream coding regions of the RCA B gene. Although pRTA115 is believed associated with the RCA precursor protein, the amino acid sequence deduced from pRTA115 for RCA matches that of ricin B for the 11 amino acids needed to complete the N-terminus. These sequences were therefore used as models for the construction of oligonucleotides encoding the mixing 11 N-terminus codons and also permit the deduction of the amino acid sequence of the 12 amino acid peptide in the single peptide precursor of RCA and, presumably, of ricin A and B.

The coding sequences of pTRB5 were disposed so as not to be expressible under the control of the lac promoter as inserted into pUC13. Therefore, pRTB5 was cut with EcoRI and PstI and the vector cleaved into several fragments with BstNI. The insert fragment was ligated under standard conditions using T4 ligase with an EcoRI/PstI digest of pUC8, another modified pBR322 vector obtained from and freely available from Messing, J., at the University of Minnesota. pUC8 has EcoRI and PstI sites which place an EcoRI/PstI insert under lac promoter control as a fusion protein with the initial 5–8 amino acids of β-galactosidase. It also contains a HindIII site immediately downstream from the PstI site. The ligation mixture was transformed into *E. coli* MM294, and transformants selected for ampicillin resistance. Plasmid DNA was isolated from successful transformants in several colonies, and analyzed by restriction site mapping. Colonies showing the appropriate restriction patterns were selected. One colony, designated pRTB151, was tested for expression of the gene for the fusion protein. On Western blot no protein band corresponding to the desired molecular weight was found, although cross-reacting proteins were produced. It was assumed that the reading frame might be improper, since this plasmid was designed to have the β-galactosidase and ricin B sequences in different phases.

H.2. Construction of the Ricin B Coding Sequence as a HindIII-Cassette - pRTB601

Figure 6:
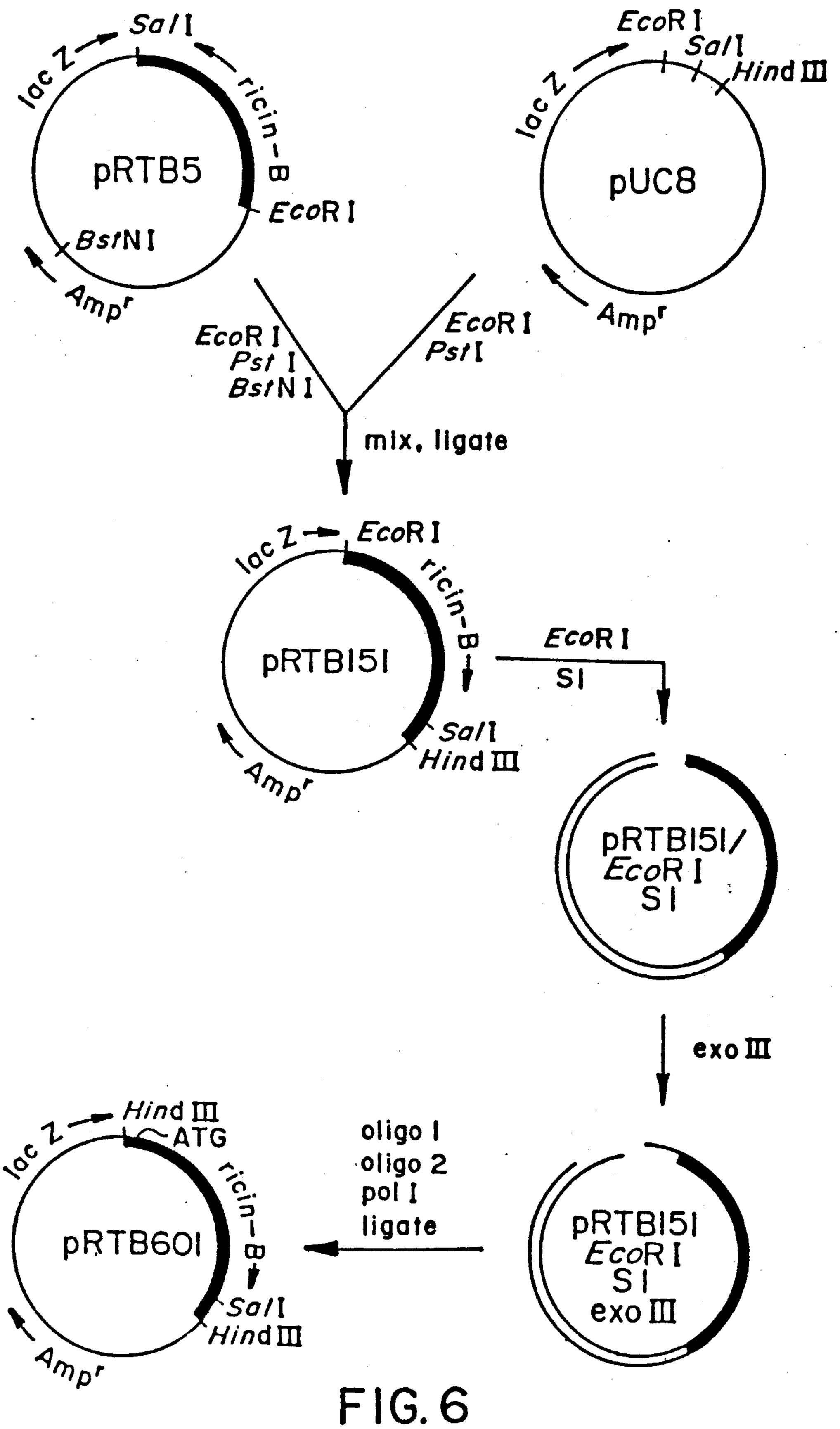
FIG. 6 shows diagrammatically the construction of pRTB601.
Figure 8:
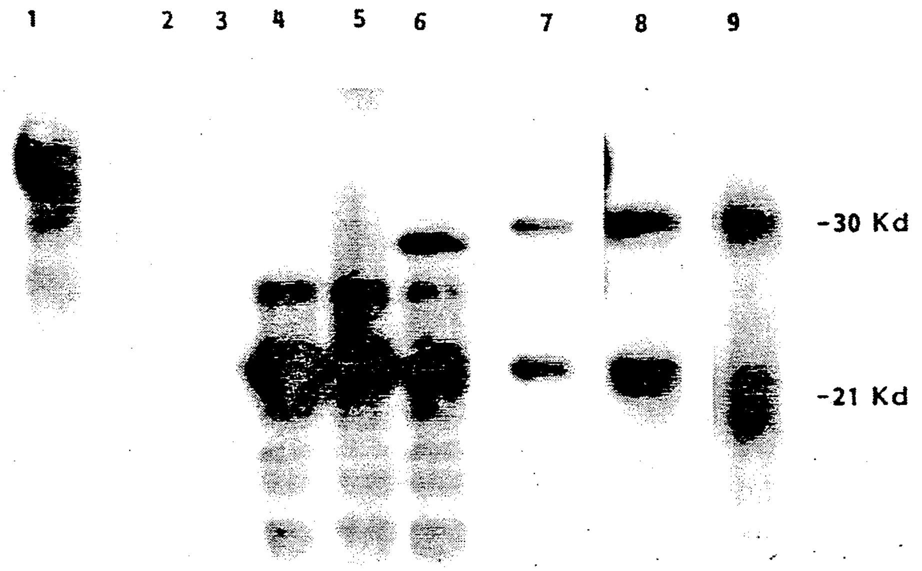
FIG. 8 shows a Western blot of extracts from *E. coli* MM294 transformed with plasmids of the invention in comparison to ricin B.
Figure 7:
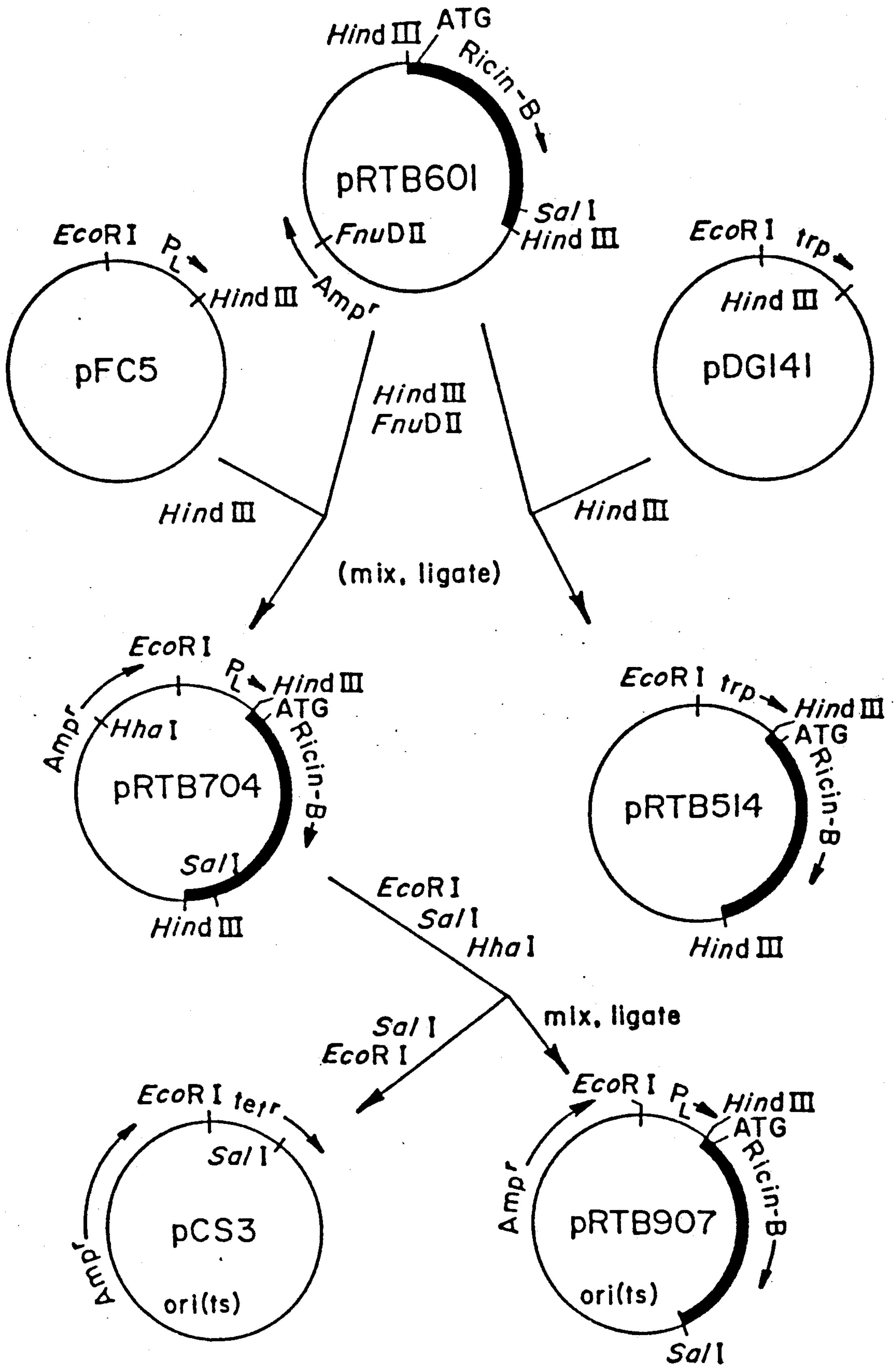
FIG. 7 shows the construction of pRTB514, pRTB704, and pRTB907.

The construction is outlined in FIG. 6.

Ten μg of pRTB151 DNA was digested to completion with EcoRI, dissolved in 60 μl Sl buffer and digested for four minutes at room temperature under conditions which remove about 1 base pair of duplex DNA per minute. DNA recovered from the foregoing buffer was dissolved in 60 μl exonuclease III buffer and digested for four minutes at room temperature. Subsequent analysis showed that the plasmid DNA had lost approximately 120 bp from each 3′ end, leaving 5′ ends available for hybridization. DNA recovered from the exonuclease III buffer was dissolved in 50 μl water and 20 μl used in the ligation/repair reaction below.

Thus, 20 μl sample (2 pmoles) was mixed with 20 pmoles each of the synthetic oligonucleotides:

```
                    Oligo 2
5'-GACCATGATAAGCTTATGGCTGATGTTTGTATGGATCC and
                 HindIII           3'TACCTAGGACTCGGGTATCACGCATAGCATCC-5'
                                                  Oligo 1
```

which have complementary sequences as shown, and wherein Oligo-2 encodes a HindIII site upstream of an ATG start codon as shown in FIG. 5A. The 5′ end of Oligo-1 is complementary to 15 bases at the 5′ end of the pRTB151 cDNA sequence as there shown and is complementary to the contiguous missing codons of the ricin B sequence. The 5′ end of Oligo-2 is complementary to the 5′ sticky end of the vector residue of the exonuclease 111 treated pRTB151.

The mixture was heated to 60° C. for five minutes in order to denature completely complementation of single-stranded DNA, cooled to 37° C. for five minutes to hybridized complementary strands, and then chilled on ice. The solution was brought to polymerase I (Klenow) buffer conditions and reacted for two hours at 12° C. in the presence of the 50 μM of the 4 dNTPs, 0.1 mM NAD, 0.3 units/μl Klenow, and 0.08 units/μl *E. coli* DNA ligase. The ligation mixture was used directly to transform competent *E. coli* MM294 and several thousand $Amp^R$ colonies found. Several hundred of these were replicated and grown on nitrocellulose filters and subjected to standard colony hybridization using $P^{32}$ kinased Oligo-2 as probe. Two clones which hybridized with the probe were analyzed by restriction analysis and sequenced, and a correct construction designated pRTB601. pRTB601 thus contains the ricin B coding sequence as a HindIII cassette. The upstream HindIII site is introduced immediately upstream of the ATG codon in Oligo-2; the downstream HindIII site arises from the pUC8 vector plasmid.

H.3. Production of Ricin B Chain Muteins by Site Specific Mutagenesis

To carry out site-specific mutagenesis of the ricin B chain, the full sequence of ricin B is ligated into an M13MP18 vector (commercially available from New England Biolabs) to serve as template for mutagenesis. Chemically synthesized purified oligodeoxyribonucleotides encoding the desired changes were then used. Plaques were selected by hybridization to the oligodeoxyribonucleotide used for mutagenesis after labeling with $^{32}$YP with polynucleotide kinase. RF-DNA from probe positive plaques was purified and ligated into an appropriate expression vector. In the present invention the DNA encoding the ricin B mutein is digested with HindIII and ligated into pPL231. pPL231 is derived from plasmid pRAP229 (ATCC 53048). Plasmid pRAP229 was digested with HindIII and KpnI to delete the ricin A sequence. A double-stranded oligonucleotide having a HindIII and a KpnI termini and an internal TAA upstream was ligated into the plasmid, and the resulting intermediate plasmid was digested with XbaI to remove a polylinker sequence upstream of the phoA promoter. The large fragment was self ligated and designated pPL231. pPL231 has been deposited in the American Type Culture Collection as ATCC 67334, deposited Mar. 4, 1987.

The oligodeoxynucleotides used to carry out the site-specific mutagenesis may be designed to encode alterations in one or more codons of the ricin B chain. Tables 15 and 16 show oligomers designed to alter the DNA encoding one or more amino acids of the galactoside binding sites of ricin B.

TABLE 15

| Amino Acid # | | | | |
|---|---|---|---|---|
| 22 | 25 | 35 | 37 | 18 19 20 21 22 23 24 25 26 27 28 29 30 31 32 33 34 35 36 37 38 39 40 |
| Asp | Asp | Gln | Trp | GGTCTATGTTGTTGATGTTAGGGATGGAAGATTCCACAACGGAAACGCAATACAGTTGTGGCCATGCAAGTCT |
| Gly | Gly | | | GGTCTATGTTGTTGATGTTAGGGATGGAAGATTCC |
| Gly | | | | GGTCTATGTTGTTGATGTTAGGG |
| | | | Ala | CGCAATACAGCTGGCGCCATGCAAG |
| | | Gly | Ala | GGAAACGCAATAGGTCTGGCGCCATGCAAG |

TABLE 16

| Amino Acid # | | | |
|---|---|---|---|
| 234 | 251 | 255 | 230 231 232 233 234 235 236 237 238 239 240 241 242 243 244 245 246 247 248 249 250 251 252 253 254 255 256 257 258 259 260 |
| | | | GGGTTGGTGTTAGATGTGAGGGCATGGGATCCGAGCC TCTCCATGGTGACCCAAACCAAATATGGTTACCATTA |
| Gly | | | GTGGGTTGGTGTTAGATGTGAGG |
| | Ala | Gly | CCCTCTCGCTGGTGACCCAGGTCAAATATGGTTACC |
| | | Gly | GGTGACCCAGGTCAAATATGGTTACC |

H.4. Expression of Ricin B Muteins

The expression of the ricin B chain according to the invention may be accomplished in a variety of host systems. In general, the ribosomes of prokaryotic cells are resistant to enzymatic inactivation by ricin toxin A and intact ricin comprising ricin toxin A and B chain. Thus, in prokaryotic cells such as *E. coli, B. subtilis* and Streptomyces species, the ricin B muteins may be expressed using any of the known expression vectors for expression in such prokaryotic hosts. The ricin B mutein according to the invention may be expressed by placing the DNA encoding the ricin B mutein in operable linkage with appropriate transcriptional and translational control sequences in an expression vector that functions in the host cell. Such expression vectors may include a secretion signal sequence that is operable in the host cell. The *B. licheniformis* penicillinase signal sequence has been demonstrated to be functional in *E. coli, B. subtilis* and *B. cerus.* The ricin B muteins according to the invention may also be expressed in a transformed prokaryotic host using a vector which comprises a DNA sequence encoding a complete ricin toxin molecule in which the B chain thereof is the mutein of the invention. The ribosome of such prokaryotic hosts as *E. coli, B. subtilis* and Streptomyces are resistant to the activity of the ricin A chain.

Ricin B chain may also be expressed independently of ricin A chain in yeast using yeast compatible expression vectors of which many are known. Yeast expression vectors in which expression of the desired gene is under control of mammalian promoters that are compatible with yeast are described in U.S. Ser. No. 618,960 filed June 11, 1984 and is incorporated herein by reference. In these constructions the DNA sequence encoding the B chain is operably linked to transcriptional and translational control signals compatible with the yeast host cell desired. A yeast compatible secretion signal sequence such as the alpha mating factor secretion signal sequence or the glucoamylase secretion leader of *Aspergillus awamori* or *Aspergillus niger* may be used as described in U.S. Pat. No. 4,794,175, which is incorporated herein by reference.

Ricin B chain muteins according to the invention may also be expressed in eukaryotic expression systems include the baculovirus expression system described in Summers et al. "Genetic Engineering of the Genome of the Autographic Californica Nuclear Polyhearosis Virus" in *Genetically Altered Viruses in the Environment,* Banburg Report #22, Cold Spring Harbor Laboratories, Cold Spring Harbor, N.Y. 1985, and various mammalian expression systems using such mammalian cells as COS cells, CV-1 cells, CHO cells and various myeloma cells such as NSI using transcriptional and translational control sequences and enhancers known in the art to be appropriate for expression in these systems.

For expression of ricin B muteins according to the invention in prokaryotic cells, *E. coli* is preferred. In general, vectors appropriate for the expression of ricin B will be under the operable control of transcriptional and translational control signals compatible with the *E. coli* cell line. Among those known in the art are the phoA, Trp, Lac and $P_L$-gene N ribosome binding site transcriptional control sequences. An exemplary *E. coli* vector is pPL231 which contains a HindIII site immediately downstream of an out-of-frame and terminated phoA secretion leader sequence which is under control of the phoA promotor and ribosome binding site. Ricin B mutein sequences in a HindIII cassette may be ligated directly into the HindIII site of pPL231 and the expression vector may be used to express ricin B or ricin B mutein in appropriate strains of *E. coli.* Such out-of-frame and terminated constructions are described in U.S. Ser. No. 837,583 filed Mar. 7, 1986 incorporated herein by reference.

H.5. Assays for Binding

The ability of ricin B chain muteins according to the invention to bind to galctose is determined by measuring the binding of ricin B chain to galactose-containing resins or surfaces coated with galactose-containing molecules or membranes which contain galactose residues. Agarose-containing resins such as Sepharose, treated with dilute acid to expose galactose residues, Bio-Gel A resins, resins such as Sepharose or Bio-Gel A coupled to saccharides such as fetuin, are suitable for binding ricin with an intact B chain or ricin B chain alone. Ricin or ricin B chain in which the galactoside binding site or sites thereof has not been modified according to the invention when passed through these columns binds to the column material. If the galactoside-binding site has been altered to produce a ricin B mutein according to the invention, binding to galactoside will be measurably diminished or eliminated.

The ability of the ricin B mutein to bind galactose is further determined by equilibrium dialysis using 3H-labeled galactose. Fluorescent polarization techniques using methylumbelliferyl galactose ay be used to measure the association of the galactose derivative with ricin B chain.

When ricin B muteins according to the invention are produced independently of ricin A chain, the ability of the ricin B mutein to interact with ricin A chain is determined by adding the ricin B mutein to a concentration of ricin A chain, deglycosylated ricin A chain, or recombinant ricin A chain that does not by itself inhibit protein synthesis in cells such as MCF-7 or HSB-2 cells. In order for the added ricin B chain to convert ricin A chain into a toxin, the galactose binding sites on ricin B chain must be capable of binding galactose-containing receptors on the surface of the target cell and the two chain must interact either covalently through a disulfide bond or non-covalently. The ability of ricin B chain muteins according to the invention encoded by DNA containing alterations in the galactose binding regions as outlined above, to convert ricin A chain into a toxin is substantially decreased or absent.

The ability of ricin B chain muteins according to the invention to interact with ricin A chain is measured by a competition assay. Native ricin B chain, having intact galactose binding sites, interacts with ricin A chain and when the ricin A-ricin B complex is added to cells, protein synthesis is prevented. Ricin B chain muteins according to the invention made from DNA in which the galactose binding residues have been modified as outlined above is added to ricin A chain before or at the same time as native ricin B chain. The ricin B chain muteins according to the invention reduce the amount of measurable protein synthesis inhibition because the ricin B mutein displaces native ricin B chain in the complex. The extent of reduction in protein synthesis is proportional to the concentration of the competing mutant ricin B chain.

If the cysteine at position 4 in ricin B chain is capable of reacting with the cysteine in ricin A chain that forms the disulfide bridge between the two chains, gel electrophoresis in non-reducing polyacrylamide gels shows the presence of a 65,000 molecular weight species. Ricin A chain has a molecular weight of about 30,000 and ricin B chain has a molecular weight of about 33,000 (both native species). Since the native species are glycosylated, their apparent size will be larger than the recombinant molecules, if they are made in non-glycosylating prokaryotic cells.

Also within the scope of the invention are conjugates of ricin in which the B chain thereof is a mutein which has reduced binding to galactosides. Ricin is covalently bound to a binding moiety that can bind to a selected target cell or tissue and which can be internalized by such target cell or tissue. Such binding moieties may be selected from a vast number of substance that bind to specific cells or tissues and include lymphokines such as interleukin-1, 2 and 3 and interferon α, β and γ; cytokines such as tumor necrosis factor and colony stimulating factors such as, CSF-1, G-CSF and GM-CSF; hormones that bind to specific hormone receptors associated with specific tissues such as the reproductive hormones that bind to ovarian tissue, e.g., leutinizing hormone; cell growth factors such as transferrin and epidermal growth factor and antibodies that bind specifically to a desired target cell or which bind to an epitope that is expressed at high level on a target cell as compared to other cell or normal cells. Such antibodies may be polyclonal or monoclonal antibodies.

H.6. Mutagenesis of Ricin B

A. Isolation of Ricin B Sequence, Orientation in Viral Vector DNA for Site-Specific Mutagenesis, Cloning Viral Vector Ricin B Muteins into Expression Vectors Plasmid pRTB601 was digested to completion with HindIII. The complete digest was used in ligation using T4 ligase under sticky end conditions to previously HindIII-digested M13MP18. After ligation, the mixture was used to transform competent *E. coli* strain DG98, ATCC Accession No. 39,768. The transformed cells were plated in the presence of 0.3 mM isopropylthiogalactoside (IPTG) obtained from Sigma Chemicals (St. Louis, Mo.) and 0.3 mg/ml X-gal on a lawn of DG98 and grown at 37° C. β-Galactosidase-negative (non-alpha complementary) white plaques were grown in liquid broth and a sample of the culture was used to purify replicative form (RF) DNA by using an alkaline-SDS miniprep protocol as described in Maniatis et al. (surpa). The presence of the insert in the anti-sense orientation was confirmed by BamHI digestion and sizing the fragment on a 1% agarose gel. Plasmids having the RTB insert in the desired orientation were reconfirmed by digestion with PstI/BglII and used for site-specific mutagenesis. They were designated M13MP18-RTBI-6.

After mutagenesis and confirmation of the mutagenized insert as described below, M13MP18 containing the mutagenized RTB DNA sequence was digested using HindIII and the sequence was ligated under sticky end conditions into plasmid pPL231. Proper orientation of the HindIII insert was determined by digestion with BamHI and/or PstI/BglII as described above.

B. Site-Specific Mutagenesis for Insertion of Unique Restriction Sites and for Alteration of Galactoside Binding Site Amino Acids in RTB

1. Insertion of SalI Site into the Amino Galactoside Binding Site

A SalI endonuclease site was inserted into the amino galactoside binding site by changing the third nucleotide encoding Val21 from T to C and the third nucleotide encoding Asp22 from T to C as shown in FIG. 10A using a 22-mer having the sequence 5'GGTCTATGTGTCGACGTTAGGG-3' according to the following general protocol.

Approximately 10 pmoles of the oligonucleotide was hybridized to about 1 pmole of single stranded DNA from M13Mp18-RTB in about 13 μl of 10 mM Tris pH 7.4, 90 mM NaCl, 10 mM $MgCl_2$ by heating to 85° C. for five minutes, followed by 45° C. for 20 minutes. The annealed mixture was chilled on ice and adjusted to 18 μl by the addition of dithiothrietol to 10 mM, each dXTP to 0.5 mM and 5 units of DNA polymerase I Klenow fragment. The reaction mixture was incubated on ice for 20 minutes followed by incubation at room temperature for one hour. The repair reaction mixture was then used to transform *E. coli* strain DG98 as above, plated onto agar plates and incubated overnight to obtain phage plaques.

Plaques were blotted using nitrocellulose filter discs and the filters were treated to lyse the cells, denature the DNA, neutralize, rinse, fix the DNA to the filter and incubate in prehybridization buffer. The oligonucleotide was end labeled with $\gamma^{32}P$ using polynucleotide kinase and hybridized to the filters at a temperature about 10° C. below the calculated melting temperature overnight. Filters were washed and subjected to autoradiography. Probe positive plaques were grown in liquid culture gel formula and characterized by SalI digestion and agarose gel sizing to confirm the presence of the expected fragments. One clone having the desired insert was isolated, purified, and retained for ligation into pPL231 with additional uninfected DG98, RF-DNA prepared as noted above.

2. Insertion of PvuII Site into the RTB Amino Galactoside Binding Site

The same method as the previous example was used to insert a PvuII site into the amino galactoside binding site of RTB by changing the third nucleotide at the codon encoding Leu48 from C to G except that a 22-mer having the following sequence was used: 5'-GCAAATCAGCTGTGGACTTTG-3' and the correct mutein was confirmed by PvuII digestion.

3. Alteration of Asp22 to Gly and Asp25 to Gly

The same method was used to change both Asp22 and Asp25 to Gly except that a 34-mer having the following sequence was used to change the second nucleotide encoding both Asp22 and Asp25 from A to G using the 34-mer: 5'-GGTCTATGTGTTGGTGTTAGGGGTGGAAGATTCC-3'.

4. Alteration of Asp22 to Gly

The same method was used to change Asp22 to Gly except that a 22-mer having the following sequence was used to change the second nucleotide from A to G: 5'-GGTCTATGTGTTGGTGTTAGGG-3'.

5. Alternation of Glu35 to Gly and Trp37 to Ala

The same method was used to change Gln35 to Gly and Trp37 to Ala except that a 30-mer having the following sequence was used to change the nucleotides encoding Gln35 and the first nucleotide encoding Leu36 from CAGT respectively to GGTC and the first two nucleotides encoding Trp37 from T and G respectively to G and C respectively: 5'-GGAAACGCAATAGGTCTGGCGCCATGCAAG-3'. A NarI and AhaII site is introduced into the sequence.

6. Alteration of Trp37 to Ala

The same method was used to change Trp37 to Ala using a 25-mer having the following sequence by changing the first nucleotide encoding Leu46 and the first two nucleotides encoding Trp37 from T, T and G respectively to C, G and C respectively: 5'-CGCAATACAGCTGGCGCCATGCAAG-3'. A NarI site is introduced into the sequence.

7. Alteration of Asp234 in the carboxyl galactoside binding site of RTB

The same method is used to change Asp234 to Gly using a 21-mer having the following sequence by changing the last nucleotide of the codon encoding Val233, the first nucleotide of Leu234 and the second nucleotide of Asp234 from G, T and A respectively to C, C and G respectively: 5'-GTGGGTTGGTCCTAGGTGTGAGG-3'. An AvrII site is introduced into the sequence.

8. Alteration of His251 to Ala and Asn255 to Gly

The same method was used to change His251 to Ala and Asn255 to Gly using a 36-mer having the following sequence by changing the first two nucleotides encoding His251 and the three nucleotides encoding Asn255 from C, A, A, A and C respectively to G. C, G, G, and T respectively: 5'-CCCTCTCGCTGGTGACCCAGGTCAAATATGGTTACC-3'. An ScrFI site is introduced into the sequence and an NcoI site in the sequence is destroyed.

9. Alteration of Asn255 to Gly

The same method is used to change Asn255 to Gly using a 26-mer having the following sequence by changing the nucleotides encoding Asn255 from A, A and C respectively to G, G and T respectively: 5'-GGTGACCCAGGTCAAATATGGTTACC-3'. An ScrFI sequence is introduced into the sequence without destroying the NcoI site.

Deposits

The materials listed below were deposited with the American Type Culture Collection, Rockville, MD, USA (ATCC). The deposits were made under the provisions of the Budapest Treaty on the International Recognition of the Deposit of Microorganisms for the Purposes of Patent Procedure and the Regulations thereunder (Budapest Treaty). Maintenance of a viable culture is assured for 30 years from date of deposit. The organism will be made available by ATCC under the terms of the Budapest Treaty, and subject to an agreement between Applicants and ATCC which assures unrestricted availability upon issuance of the pertinent U.S. patent. Availability of the deposited strain is not to be construed as a license to practice the invention in contravention of the rights granted under the authority of any government in accordance with its patent laws.

| Plasmid | Deposit Date | CMCC# | ATCC# |
|---|---|---|---|
| pDG144 | 1/13/84 | — | 39579 |
| pFC5 | 9/14/84 | 1935 | 39864 |
| pCS3 | 6/3/82 | — | 39142 |
| pTRP3 | 12/18/84 | 1731 | 39946 |
| pDG141 | 1/24/84 | — | 39588 |
| pRTB704 | 9/24/84 | 1951 | 39865 |
| pRAP229 | 3/8/85 | 2218 | 53048 |
| *B. thuringiensis* | | 1615 | 39756 |
| pPL231 | 3/4/87 | 2913 | |

What is claimed is:

1. DNA encoding a ricin B mutein that exhibits decreased affinity for galactosides, comprising the substitution of Asn255 to either Leu or lie and the substitution of either Tyr248 or His255 to either Gly or Ala.

2. DNA encoding a ricin B mutein that exhibits decreased affinity for galactosides, comprising the substitution of Tyr248 to Gly, Ala, or Ser.

3. DNA encoding a ricin B mutein that exhibits decreased affinity for galactosides, comprising the substitution of His251 to Gly, Ala, Asp, Glu, or Lys.

4. DNA encoding a ricin B mutein that exhibits decreased affinity for galactosides, comprising the substitution of Asn255 to Gly, Ala, Glu, Gln, Asp, or Cys.

5. Recombinant host cells transformed with an expression vector comprising a DNA sequence encoding mutein of ricin B operably linked to control sequences compatible with a recombinant host cell, said mutein being selected from the group consisting of substituting Asn255 to either Leu, Ile, Gly, Ala, Glu, Gln, Asp, or Cys; Tyr248 or His251 to either Gly, or Ala; Tyr248 to Gly, Ala, or Ser; His251 to Gly, Ala, Asp, Glu, or Lys.

6. A replicable, recombinant expression vector effective in expressing the DNA sequence encoding mutein of ricin B, which mutein comprises substitutions selected from the group consisting of Asn255 to either Leu or Ile and the substitution of either Tyr248 or His251 to either Gly, or Ala.

7. A ricin B mutein that exhibits decreased affinity for galactosides, comprising the substitution of Asn255 to either Leu or Ile and the substitution of either Tyr248 or His255 to either Gly or Ala.

8. A ricin B mutein that exhibits decreased affinity for galactosides, comprising the substitution of Try248 to Gly, Ala, or Ser.

9. A ricin B mutein that exhibits decreased affinity for galactosides, comprising the substitution of His251 to Gly, Ala, Asp, Glu, or Lys.

10. A ricin B mutein that exhibits decreased affinity for galactosides, comprising the substitution of Asn255 to Gly, Ala, Blu, Gln, Asp, or Cys.

11. A mutein of ricin B, wherein at least one of the amino acids of positions 37 and 248 is deleted or substituted with a naturally occurring amino acid.

* * * * *